US011730799B2

United States Patent
Lubaroff et al.

(10) Patent No.: US 11,730,799 B2
(45) Date of Patent: Aug. 22, 2023

(54) CANCER VACCINES AND METHODS OF PRODUCING AND USING SAME

(71) Applicants: UNIVERSITY OF IOWA RESEARCH FOUNDATION, Iowa City, IA (US); THE UNITED STATES GOVERNMENT DEPARTMENT OF VETERANS AFFAIRS, Washington, DC (US)

(72) Inventors: David M. Lubaroff, Iowa City, IA (US); Delbert L. Harris, Ames, IA (US)

(73) Assignees: UNIVERSITY OF IOWA RESEARCH FOUNDATION, Iowa City, IA (US); THE UNITED STATES GOVERNMENT DEPARTMENT OF VETERANS AFFAIRS, Washington, DC (US)

( * ) Notice: Subject to any disclaimer, the term of this patent is extended or adjusted under 35 U.S.C. 154(b) by 45 days.

(21) Appl. No.: 17/304,953

(22) Filed: Jun. 29, 2021

(65) Prior Publication Data
US 2021/0322529 A1  Oct. 21, 2021

Related U.S. Application Data

(63) Continuation of application No. 16/606,578, filed on Oct. 18, 2019, now abandoned.

(51) Int. Cl.
A61K 39/00 (2006.01)
A61P 35/00 (2006.01)
C12N 7/00 (2006.01)

(52) U.S. Cl.
CPC ........... *A61K 39/001193* (2018.08); *A61K 39/001194* (2018.08); *A61K 39/001195* (2018.08); *A61P 35/00* (2018.01); *C12N 7/00* (2013.01); *A61K 2039/5256* (2013.01); *A61K 2039/5258* (2013.01); *A61K 2039/545* (2013.01); *A61K 2039/884* (2018.08); *C12N 2710/10341* (2013.01); *C12N 2770/36123* (2013.01); *C12N 2770/36143* (2013.01)

(58) Field of Classification Search
CPC .... A61K 39/001193; A61K 39/001194; A61K 39/001195; A61K 2039/5256; A61K 2039/5258; A61K 2039/545; A61K 2039/884; A61K 2039/51; A61P 35/00; C12N 7/00; C12N 2710/10341; C12N 2770/36123; C12N 2770/36143; C12N 2710/10343
See application file for complete search history.

(56) References Cited

U.S. PATENT DOCUMENTS

| 2005/0208020 | A1 | 9/2005 | Doolan et al. |
| 2005/0266550 | A1 | 12/2005 | Rayner et al. |
| 2006/0177819 | A1* | 8/2006 | Smith ............. A61P 35/00 435/69.3 |
| 2012/0213813 | A1 | 8/2012 | Smith et al. |
| 2016/0375115 | A1 | 12/2016 | Binder et al. |

FOREIGN PATENT DOCUMENTS

EP    1069908 B1    2/2010

OTHER PUBLICATIONS

Ng KL. The Etiology of Prostate Cancer. In: Bott SRJ, Ng KL, editors. Prostate Cancer [Internet]. Brisbane (AU): Exon Publications; May 27, 2021. Chapter 2. Available from: https://www.ncbi.nlm.nih.gov/books/NBK571322/doi: 10.36255/exonpublications.prostatecancer.etiology.2021. (Year: 2021).*
Doehn C, Böhmer T, Kausch I, Sommerauer M, Jocham D. Prostate cancer vaccines: current status and future potential. BioDrugs. 2008;22(2):71-84. (Year: 2008).*
Uematsu Y, Vajdy M, Lian Y, Perri S, Greer CE, Legg HS, Galli G, Saletti G, Otten GR, et al. Lack of interference with immunogenicity of a chimeric alphavirus replicon particle-based influenza vaccine by preexisting antivector immunity. Clin Vaccine Immunol. Jul. 2012;19(7):991-8. (Year: 2012).*
Somanathan S, Calcedo R, Wilson JM. Adenovirus-Antibody Complexes Contributed to Lethal Systemic Inflammation in a Gene Therapy Trial. Mol Ther. Mar. 4, 2020;28(3):784-793. Epub Feb. 7, 2020. (Year: 2020).*
Barouch DH, Pau MG, Custers JH, Koudstaal W, Kostense S, Havenga MJ, Truitt DM, Sumida SM, Kishko MG, Arthur JC, Korioth-Schmitz B, et al. Immunogenicity of recombinant adenovirus serotype 35 vaccine in the presence of pre-existing anti-Ad5 immunity. J Immunol. May 15, 2004;172(10):6290-7. (Year: 2004).*
Jung SY, Kang KW, Lee EY, Seo DW, Kim HL, Kim H, Kwon T, et al. Heterologous prime-boost vaccination with adenoviral vector and protein nanoparticles induces both Th1 and Th2 responses against Middle East respiratory syndrome coronavirus. Vaccine. Jun. 7, 2018;36(24):3468-3476. Epub May 5, 2018. (Year: 2018).*
Fausther-Bovendo H, Kobinger GP. Pre-existing immunity against Ad vectors: humoral, cellular, and innate response, what's important? Hum Vaccin Immunother. 2014;10(10):2875-84. (Year: 2014).*

(Continued)

*Primary Examiner* — Rachel B Gill
(74) *Attorney, Agent, or Firm* — McKee, Voorhees & Sease, PLC

(57) ABSTRACT

A method of vaccinating a subject is provided, where a cancer protective response is produced. A first vaccine comprises an adenovirus vector comprising at least one nucleic acid molecule that produces a cancer protective response is administered, followed by one or more second vaccines comprising an alphavirus replicon particle comprising RNA comprising or produced from the nucleic acid molecule. In an embodiment the cancer is prostate cancer.

15 Claims, 4 Drawing Sheets
Specification includes a Sequence Listing.

(56) References Cited

OTHER PUBLICATIONS

Lu S. Heterologous prime-boost vaccination. Curr Opin Immunol. Jun. 2009;21(3):346-51. Epub Jun. 6, 2009. (Year: 2009).*
Ljungberg K, Liljeström P. Self-replicating alphavirus RNA vaccines. Expert Rev Vaccines. Feb. 2015;14(2):177-94. Epub Oct. 1, 2014. (Year: 2014).*
Agnihothram S, Menachery VD, Yount BL Jr,, Lindesmith LC, Scobey T, Whitmore A, Scháfer A, Heise MT, Baric RS. Development of a Broadly Accessible Venezuelan Equine Encephalitis Virus Replicon Particle Vaccine Platform. J Virol. May 14, 2018;92(11):e00027-18. (Year: 2018).*
Riabovv, Tretyakova I, Alexander RB, Pushko P, Klyushnenkova EN. Anti-tumor effect of the alphavirus-based virus-like particle vector expressing prostate-specific antigen in a HLA-DR transgenic mouse model of prostate cancer. Vaccine. Oct. 5, 2015;33(41):5386-5395. Epub Aug. 28, 2015. (Year: 2015).*
Kaufman HL, Wang W, Manola J, DiPaola RS, Ko YJ, Sweeney C, Whiteside TL, Schlom J, Wilding G, Weiner LM. Phase II randomized study of vaccine treatment of advanced prostate cancer (E7897): a trial of the Eastern Cooperative Oncology Group. J Clin Oncol. Jun. 1, 2004;22(11):2122-32. (Year: 2004).*
Geary et al., "Proposed mechanisms of action for prostate cancer vaccines", Nature Reviews, Urology, Advance Online Publication www.nature.com/nrurol, 12 pages, Feb. 12, 2013.
GenBank: X14810.1, "Human DNA for prostate specific antigen (PSA)", https://www.ncbi.nlm.nih.gov/35732, 3 pages, Nov. 14, 2006.
Jiang et al., "Sterile Protection against Plasmodium knowlesi in Rhesus Monkeys from a Malaria Vaccine: Comparison of Heterologous Prime Boost Strategies", PLoS One, vol. 4, Issue 8, 12 pages, Aug. 2009.
Karan et al., "Paradoxical enhancement of CD8 T cell-dependent anti-tumor protection despite reduced CD8 T cell responses with addition of a TLR9 agonist to a tumor vaccine", Int. J. Cancer, vol. 121, pp. 1520-1528, Apr. 24, 2007.
Klobeck et al., "Genomic sequence of human prostate specific antigen (PSA)", Nucleic Acids Research, vol. 17, No. 10, 1 page, Apr. 12, 1989.
Lubaroff et al., "Phase I Clinical Trial of an Adenovirus/Prostate-Specific Antigen Vaccine for Prostate Cancer: Safety and Immunologic Results", Clin. Cancer Res., vol. 15(23), pp. 7375-7380, Dec. 1, 2009.
Lubaroff et al., "Vaccine Immunotherapy for prostate cancer: from mice to men", Immunol Res., vol. 59, pp. 229-235, 2014.
Lubaroff et al., "Decreased cytotoxic T cell activity generated by co-administration of PSA vaccine and CpG ODN is associated with increased tumor protection in a mouse model of prostate cancer", Vaccine, vol. 24, pp. 6155-6162, Apr. 17, 2006.
Lubaroff, David M., "Prostate cancer vaccines in clinical trials", Vaccine, vol. 11(7), pp. 857-868, 2012.
Lubaroff et al., "Clinical Protocol: Phase I Study of an Adenovirus/Prostate-Specific Antigen Vaccine in Men with Metastatic Prostate Cancer", Human Gene Therapy, vol. 17, pp. 220-229, Feb. 2006.
Lubaroff, David M., "Prime and boost vaccination against HER2/neu in breast cancer", Dissertation 2004.
Siemens et al., "Cutting Edge: Restoration of the Ability to Generate CTL in Mice Immune to Adenovirus by Delivery of Virus in a Collagen-Based Matrix", Journal of Immunology, pp. 731-735, 2001.
Thorner et al., "Immunogenicity of Heterologous Recombinant Adenovirus Prime-Boost Vaccine Regimens Is Enhanced by Circumventing Vector Cross-Reactivity", Journal of Virology, vol. 80, No. 24, pp. 12009-12016, Dec. 2006.
Uhlman et al., "Prostate cancer vaccines in combination with additional treatment modalities", Immunol. Res., vol. 59, pp. 236-242, 2014.
International Searching Authority in connection with PCT/US2018/027093 filed Apr. 11, 2018, "Written Opinion of the International Searching Authority", 7 pages, dated Jul. 3, 2018.
Elzey et al., "Immunization with Type 5 Adenovirus Recombinant for a Tumor Antigen in Combination with Recombinant Canarypox Virus (ALVAC) Cytokine Gene Delivery Induces Destruction of Established Prostate Tumors", Int. J. Cancer, vol. 94, pp. 842-849, Jul. 23, 2001.
Sweeney et al., "Oncolytic adenovirus-mediated therapy for prostate cancer", Oncolytic Virotherapy, vol. 5, pp. 45-57, 2016.
Lubaroff et al., "An ongoing phase II trial of an adenovirus vaccine for prostate cancer", Amer Assoc Cancer Res Annual Meeting, 2012.

* cited by examiner

CANCER VACCINES AND METHODS OF PRODUCING AND USING SAME

REFERENCE TO RELATED APPLICATION

This application is a continuation of and claims priority to previously filed U.S. Ser. No. 16/606,578, filed Oct. 18, 2019, which claims priority to PCT/2018/027093, filed Apr. 11, 2018, and previously filed and application U.S. Ser. No. 62/487,326, filed Apr. 19, 2017, the contents of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 29, 2018, is named LUBAROFF_P12169WO00_SEQ_LISTING_ST25.txt and is 8,014 bytes in size.

BACKGROUND

To date cancer vaccine protocols have met with challenges that have limited efficacy. Whole cell vaccines, peptide or whole protein vaccines or antigen specific vaccines have been attempted but have unfortunately have shown limited impact on inhibiting cancer growth or elimination. Prostate cancer is an example. Prostate cancer is the number one non-skin cancer in males and the second leading cause of cancer deaths, with an estimated 220,800 men diagnosed in 2015 and 27,540 deaths predicted in the United States. Globally, the 2012 data (the last published information) reported that there were 1,111,700 new cases and 307,500 deaths. For many prostate cancer patients, primary therapies of surgery or radiation are not curative and the cancer recurs. Subsequent therapeutic options are effective in reducing the amount of tumor, but ultimately there is a breakthrough within an average of 2 years. Additional therapies have been developed, but they usually only provide an additional 2 to 4 months survival advantage. Eventually patients cease to respond to any treatment, leading to their death. Thus, new and alternative treatments are required.

Because there is no cure for recurrent prostate and other cancers, although newer treatments have been shown to extend survival by a modest number of months, the unmet need is for a therapy or therapies that either significantly extend life or cure the disease. Extension of life must also include a good quality of life. All of the current therapies are associated with significant adverse events that reduce quality of life. The new treatment(s) should also carry a reasonable cost to the patient. Current treatment costs are close to $100,000 per patient.

SUMMARY

Provided here are cancer vaccines, which in an embodiment provide for administration to a subject in need thereof. A vaccine comprises a nucleic acid molecule that produces a cancer protective response in a patient. An embodiment provides the vaccine may be delivered by an adenovirus vector, by an alphavirus vector and in a preferred embodiment, both an adenovirus and an alphavirus vector replicon particle vaccine is administered to the patient. In an embodiment the adenovirus vector comprising the antigenic nucleic acid molecule is administered to the patient, followed by administration of an alphavirus vector comprising the antigenic nucleic acid molecule. An embodiment provides the adenovirus vector is administered first, followed by administration of the alphavirus vector replicon particle vaccine in about 14 days.

DESCRIPTION

Figure 1:
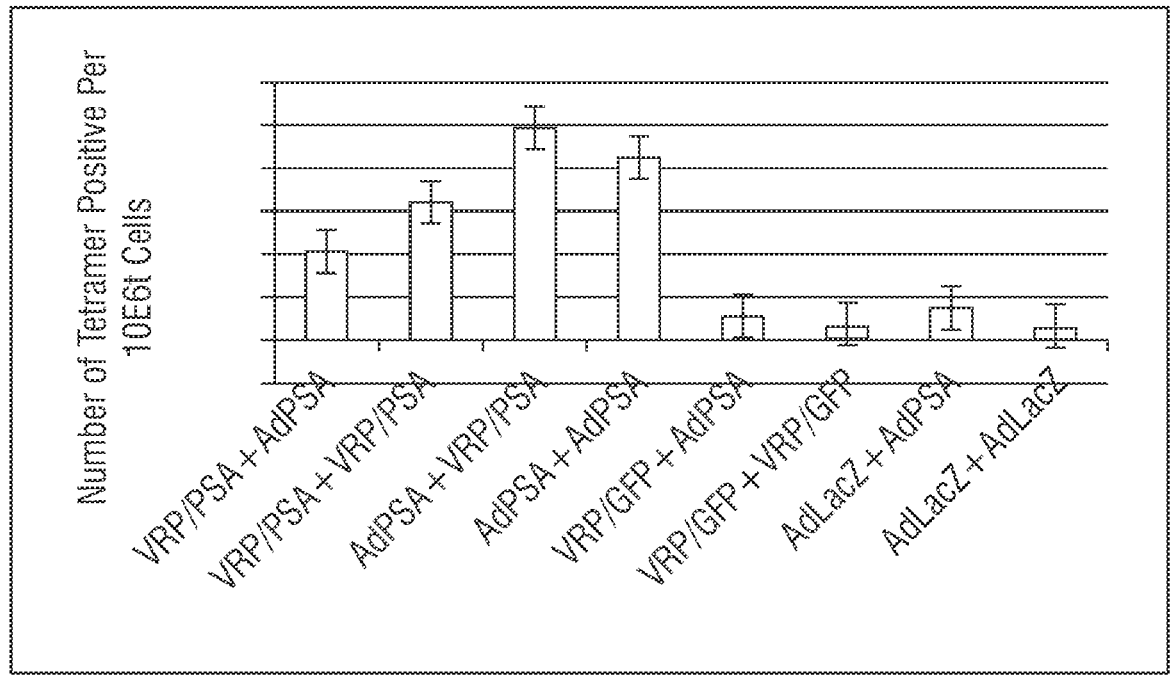
FIG. 1 is a graph showing the number of tetramer positive cells produced in response to differing vaccination administration. VRP refers to alphavirus replicon particle; PSA refers to prostate specific antigen; AdPSA refers to adenovirus vector with PSA; AdLacZ refers to a control adenovirus vector carrying the lacZ gene for a non-specific antigen (β-galactosidase).

Provided here are cancer vaccines that are safe, highly effective, can be prepared in a short amount of time, usually within 4 to 6 weeks, and provided to patients at a cost far less than currently available cancer treatments. Estimates of costs of the vaccine and with the absence of blood processing, are anticipated to be considerably less than the $100,000 price of the currently available prostate cancer vaccine. An embodiment of the vaccine and process of administration provides for a replication deficient adenovirus vector (Ad) comprising at least one cancer protective nucleic acid molecule that when administered produces a cancer protective response in the patient. The administration of this vaccine is followed by administration of one or more vaccines comprising a replication deficient alphavirus replicon particle (VRP or RP) comprising the at least one cancer protective nucleic acid molecule. When administering a "prime" vaccine of the Ad vector vaccine followed by one or more "boosting" vaccinations of the VRP vaccine, a synergistic enhancement of cancer protection is provided to the patient. In an embodiment, the nucleic acid molecule is a prostate cancer protective nucleic acid molecule. A further embodiment provides that the prime vaccine is followed by a booster vaccine within about 14 days. Additional booster injections will occur at 14 day intervals. An embodiment provides for one, two, three, four, five, six or more booster vaccinations. Results in preclinical studies demonstrated tumor eradication using three boosters. In still further embodiments, the cancer protective response may be reduction in growth or destruction of cancer tumors and may include elimination of tumors. An embodiment provides for destruction of 20%, 30%, 40%, 50%, 60%, 70%, 80%, 90% up to 100% of tumors.

The processes and vaccines described here may be used in connection with a cancer in which a nucleic acid molecule can be identified that has a cancer protective effect. The term "cancers," as used herein, refers to the commonly understood spectrum of diseases including, but not limited to, solid tumors, such as cancers of the breast, respiratory tract, brain, reproductive organs, digestive tract, urinary tract, eye, liver, skin, head and neck, thyroid, parathyroid and their distant metastases, and also includes lymphomas, sarcomas, and leukemias. Examples of breast cancer include, but are not limited to invasive ductal carcinoma, invasive lobular carcinoma, ductal carcinoma in situ, and lobular carcinoma in situ. Examples of cancers of the respiratory tract include but are not limited to small-cell and non-small-cell lung carcinoma, as well as bronchial adenoma and pleuropulmonary blastoma. Examples of brain cancers include but are not limited to brain stem and hypophthalmic glioma, cerebellar and cerebral astrocytoma, medulloblastoma, ependymoma, as well as neuroectodermal and pineal tumor. Tumors of the male reproductive organs include but are not limited to prostate and testicular cancer. Tumors of the female reproductive organs include, but are not limited to endometrial, cervical, ovarian, vaginal, and vulvar cancer, as well as sarcoma of the uterus. Tumors of the digestive tract include, but are not limited to anal, colon, colorectal, esophageal, gallbladder, gastric, pancreatic, rectal, small intestine, and salivary gland cancers. Tumors of the urinary tract include, but are not limited to bladder, penile, kidney, renal pelvis, ureter, and urethral cancers. Eye cancers include but are not limited to intraocular melanoma and retinoblastoma. Examples of liver cancers include but are not limited to hepatocellular carcinoma (liver cell carcinomas with or without fibrolamellar variant), cholangiocarcinoma (intrahepatic bile duct carcinoma), and mixed hepatocellular cholangiocarcinoma. Skin cancers include, but are not limited to squamous cell carcinoma, Kaposi's sarcoma, malignant melanoma, Merkel cell skin cancer, and non-melanoma skin cancer. Head-and-neck cancers include but are not limited to laryngeal/hypopharyngeal/nasopharyngeal/oropharyngeal cancer, and lip and oral cavity cancer. Lymphomas include, but are not limited to AIDS-related lymphoma, non-Hodgkin's lymphoma, cutaneous T-cell lymphoma, Hodgkin's disease, and lymphoma of the central nervous system. Sarcomas include but are not limited to sarcoma of the soft tissue, fibrosarcoma, osteosarcoma, malignant fibrous histiocytoma, lymphosarcoma, and rhabdomyosarcoma. Leukemias include, but are not limited to acute myeloid leukemia, acute lymphoblastic leukemia, chronic lymphocytic leukemia, chronic myelogenous leukemia, and hairy cell leukemia. Cancers also specifically include, but are not limited to, chronic myeloid leukemia (CML), acute myeloid leukemia (AML), cutaneous T cell lymphoma (CTCL), cutaneous T cell lymphoma (CTCL), acute T lymphoblast leukemia (ALL), MDR acute T lymphoblast leukemia (MDR ALL), large B-lymphocyte non-Hodgkin's lymphoma, leukemic monocyte lymphoma, epidermal squamous carcinoma, epithelial lung adenocarcinoma, liver hepatocellular carcinoma, colorectal carcinoma, breast adenocarcinoma, brain glioblastoma, prostate adenocarcinoma, gastric carcinoma and other cancerous tissues. These disorders have been characterized in humans, but also exist with a similar etiology in other mammals and can be treated by administering the methods and vaccines here. Examples, without intending to be limiting, of currently identified tumor-associated antigens in non-prostate cancers are Her-2, MUC-1, and CD20.

Any nucleic acid molecule that provides a cancer protective response may be used in the processes here. The terms "protecting", "protection", "protective response" as used herein, are intended to mean that the subject morbidity or mortality is improved, and/or the cancer cell or tumor growth or adverse impact on the subject is reduced or eliminated. The nucleic acid molecule may be associated with production of an antigen. In another embodiment the response may or may not produce antibodies. Where administered prophylactically, there is a reduction in incidence or growth of the cancer. Such protective response may be observed or measured in a myriad of ways. By way of example without limitation, where referring to prostate cancer, one may measure total PSA values, PSA doubling time, time to progression, reduction or elimination of tumors and/or tumor growth, and overall survival.

In an embodiment of the processes here, the cancer is prostate cancer. The nucleic acid molecule may be selected from any molecule that can provide a protective response, and can include for example, prostate specific antigen (PSA) (See for example Klobeck et al. "Genomic sequence of human prostate specific antigen (PSA)" *Nuc. Acids Research* Vol. 17 No. 10 (1989) EMBL accession No. X14810), prostate stem cell antigen (PSCA; examples include Reiter et al. "Prostate stem cell antigen: a cell surface marker overexpressed in prostate cancer *Proc. Natl. Acad. Sci. U.S.A.* 95(4), 1735-1740 (1998): GenBank Ref No. AAC39607.1), prostate acid phosphatase (PAP; examples include Sharief et al. "Human prostatic acid phosphatase: cDNA cloning, gene mapping and protein sequence homology with lysosomal acid phosphatase" *Biochem. Biophys. Res. Commun.* 160 (1), 79-86 (1989); GenBank Ref No. AAA60022.1) and prostate specific membrane antigen (PSMA; examples include Israeli et al. "Molecular cloning of a complementary DNA encoding a prostate-specific membrane antigen" Cancer Res. 53(2), 227-230 (1993); Gen Bank Ref No. AAA60209.1). All or fragments of a molecule that provides a cancer protective response may be used in the processes here.

Further, the vaccine may be monovalent or polyvalent and more than one cancer protective nucleic acid molecule may be provided in the vaccine; either more than one of the selected nucleic acid molecule, or different nucleic acid molecules. The prime and boost vaccine will include at least one nucleic acid molecule that is the same.

The methods disclosed include any useful variation of a sequence that provides a cancer protective response. For example, methods of alignment of sequences for comparison are well known in the art. Thus, the determination of percent identity between any two sequences can be accomplished using a mathematical algorithm.

Optimal alignment of sequences for comparison can use any means to analyze sequence identity (homology) known in the art, e.g., by the progressive alignment method of termed "PILEUP" (Morrison, (1997) *Mol. Biol. Evol.* 14:428-441, as an example of the use of PILEUP); by the local homology algorithm of Smith & Waterman (*Adv. Appl. Math.* 2: 482 (1981)); by the homology alignment algorithm of Needleman & Wunsch (*J. Mol. Biol.* 48:443-453 (1970)); by the search for similarity method of Pearson (*Proc. Natl. Acad. Sci. USA* 85: 2444 (1988)); by computerized implementations of these algorithms (e.g., GAP, BEST FIT, FASTA, and TFASTA in the Wisconsin Genetics Software Package, Genetics Computer Group, 575 Science Dr., Madison, Wis.); ClustalW (CLUSTAL in the PC/Gene program by Intelligenetics, Mountain View, Calif., described by, e.g., Higgins (1988), *Gene* 73: 237-244; Corpet (1988), *Nucleic Acids Res.* 16:10881-10890; Huang, *Computer Applications in the Biosciences* 8:155-165 (1992); and Pearson (1994), *Methods in Mol. Biol.* 24:307-331); Pfam (Sonnhammer (1998), *Nucleic Acids Res.* 26:322-325); TreeAlign (Hein (1994), *Methods Mol. Biol.* 25:349-364); MEG-ALIGN, and SAM sequence alignment computer programs; or, by manual visual inspection. Another example of algorithm that is suitable for determining sequence similarity is the BLAST algorithm, which is described in Altschul et al, (1990) *J. Mol. Biol.* 215: 403-410. The BLAST programs (Basic Local Alignment Search Tool) of Altschul, S. F., et al., searches under default parameters for identity to sequences contained in the BLAST "GENEMBL" database. A sequence can be analyzed for identity to all publicly available DNA sequences contained in the GENEMBL database using the BLASTN algorithm under the default parameters.

Software for performing BLAST analyses is publicly available through the National Center for Biotechnology Information; see also Zhang (1997), *Genome Res.* 7:649-656 for the "PowerBLAST" variation. This algorithm involves first identifying high scoring sequence pairs (HSPs) by identifying short words of length W in the query sequence that either match or satisfy some positive valued threshold score T when aligned with a word of the same length in a database sequence. T is referred to as the neighborhood word score threshold (Altschul et al (1990), *J. Mol. Biol.* 215: 403-410). These initial neighborhood word hits act as seeds for initiating searches to find longer HSPs containing them. The word hits are extended in both directions along each sequence for as far as the cumulative alignment score can be increased. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff (1992), *Proc. Natl. Acad. Sci. USA* 89:10915-10919) alignments (B) of 50, expectation (E) of 10, M=5, N=−4, and a comparison of both strands. The term BLAST refers to the BLAST algorithm which performs a statistical analysis of the similarity between two sequences; see, e.g., Karlin (1993), *Proc. Natl. Acad. Sci. USA* 90:5873-5787. One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

In an embodiment, GAP (Global Alignment Program) can be used. GAP uses the algorithm of Needleman and Wunsch (*J. Mol. Biol.* 48:443-453, 1970) to find the alignment of two complete sequences that maximizes the number of matches and minimizes the number of gaps. Default gap creation penalty values and gap extension penalty values in the commonly used Version 10 of the Wisconsin Package® (Accelrys, Inc., San Diego, Calif.) for protein sequences are 8 and 2, respectively. For nucleotide sequences the default gap creation penalty is 50 while the default gap extension penalty is 3. Percent Similarity is the percent of the symbols that are similar. Symbols that are across from gaps are ignored. A similarity is scored when the scoring matrix value for a pair of symbols is greater than or equal to 0.50, the similarity threshold. A general purpose scoring system is the BLOSUM62 matrix (Henikoff and Henikoff (1993), *Proteins* 17: 49-61), which is currently the default choice for BLAST programs. BLOSUM62 uses a combination of three matrices to cover all contingencies. Altschul, *J. Mol. Biol.* 36: 290-300 (1993), herein incorporated by reference in its entirety and is the scoring matrix used in Version 10 of the Wisconsin Package® (Accelrys, Inc., San Diego, Calif.) (see Henikoff & Henikoff (1989) *Proc. Natl. Acad. Sci. USA* 89:10915).

The following terms are used to describe the sequence relationships between two or more nucleic acids or polynucleotides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length promoter sequence, or the complete promoter sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to accurately reflect the similarity to a reference sequence due to inclusion of gaps in the polynucleotide sequence a gap penalty is typically introduced and is subtracted from the number of matches.

(c) As used herein, "sequence identity" or "identity" in the context of two nucleic acid sequences makes reference to the residues in the two sequences that are the same when aligned for maximum correspondence over a specified comparison window.

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison, and multiplying the result by 100 to yield the percentage of sequence identity.

Identity to the sequence of described would mean a polynucleotide sequence having at least 65% sequence identity, more preferably at least 70% sequence identity, more preferably at least 75% sequence identity, more preferably at least 80% identity, more preferably at least 85% 86%, 87%, 88%, 89%, 90%, 91%, 92%, 93%, 94%, 95%, 96%, 97%, 98%, 99% sequence identity.

When referring to hybridization techniques, all or part of a known nucleotide sequence can be used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the DNA sequences. Methods for preparation of probes for hybridization and for construction of cDNA and genomic libraries are generally known in the art and are disclosed (Sambrook et al., 2001).

For example, the sequences disclosed herein, or one or more portions thereof, may be used as a probe capable of specifically hybridizing to corresponding sequences. To achieve specific hybridization under a variety of conditions, such probes include sequences that are unique among the sequences to be screened and are preferably at least about 10 nucleotides in length, and most preferably at least about 20 nucleotides in length. Such sequences may alternatively be used to amplify corresponding sequences from a chosen plant by PCR. This technique may be used to isolate sequences from a desired plant or as a diagnostic assay to determine the presence of sequences in a plant. Hybridization techniques include hybridization screening of DNA libraries plated as either plaques or colonies (Sambrook et al., (2001) *Molecular Cloning—A Laboratory Manual* (Third ed.) Vol. 1-3, Cold Spring Harbor Laboratory, Cold Spring Harbor Press, NY,).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 0.1% SDS at 37° C., and a wash in 0.1×SSC at 60 to 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m = 81.5° C. + 16.6 (\log M) + 0.41 (\% GC) - 0.61 (\% \text{form}) - 500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with 90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen (1993) *Laboratory Techniques in Biochemistry and Molecular Biology*—Hybridization with Nucleic Acid Probes, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (2001) *Molecular Cloning: A Laboratory Manual* ($3^{rd}$ ed., Cold Spring Harbor Laboratory Press, Plainview, N.Y.) and Haymes et al. (1985) In: *Nucleic Acid Hybridization*, a Practical Approach, IRL Press, Washington, D.C.

In general, sequences that correspond to the nucleotide sequences described and hybridize to the nucleotide sequence disclosed herein will be at least 50% homologous, 70% homologous, and even 85%, 86%, 87%, 88%, 89%, 90%, 91%, 92%, 93%, 94%, 95%, 96%, 97%, 98%, 99% homologous or more with the disclosed sequence. That is, the sequence similarity between probe and target may range, sharing at least about 50%, about 70%, and even about 85% or more sequence similarity.

Unless otherwise indicated, a particular nucleic acid sequence also implicitly encompasses conservatively modified variants thereof (e.g. degenerate codon substitutions) and complementary sequences as well as the sequence explicitly indicated. The term conservatively modified variants applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are silent variations and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide is implicit in each described polypeptide sequence and is within the scope of the products and processes described.

As used herein, the terms nucleic acid or polynucleotide refer to deoxyribonucleotides or ribonucleotides and polymers thereof in either single- or double-stranded form. As such, the terms include RNA and DNA, which can be a gene or a portion thereof, a cDNA, a synthetic polydeoxyribonucleic acid sequence, or the like, and can be single-stranded or double-stranded, as well as a DNA/RNA hybrid. Furthermore, the terms are used herein to include naturally-occurring nucleic acid molecules, which can be isolated from a cell, as well as synthetic molecules, which can be prepared, for example, by methods of chemical synthesis or by enzymatic methods such as by the polymerase chain reaction (PCR). Unless specifically limited, the terms encompass nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g. degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) *Nucleic Acid Res.* 19:5081; Ohtsuka et al. (1985) *J Biol. Chem.* 260:2605-2608; Rossolini et al. (1994) *Mol. Cell. Probes* 8:91-98). The term nucleic acid is used interchangeably with gene, cDNA, and mRNA encoded by a gene.

As used herein, a nucleotide segment is referred to as operably linked when it is placed into a functional relationship with another DNA segment. For example, DNA for a signal sequence is operably linked to DNA encoding a polypeptide if it is expressed as a preprotein that participates in the secretion of the polypeptide; a promoter or enhancer is operably linked to a coding sequence if it stimulates the transcription of the sequence. Operably linked elements may be contiguous or non-contiguous. When used to refer to the joining of two protein coding regions, by operably linked it is intended that the coding regions are in the same reading frame. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette can include one or more enhancers in addition to the promoter. By enhancer is intended a cis-acting sequence that increases the utilization of a promoter. Such enhancers can be native to a gene or from a heterologous gene. Further, it is recognized that some promoters can contain one or more enhancers or enhancer-like elements. An example of one such enhancer is the 35S enhancer, which can be a single enhancer, or duplicated. See for example, McPherson et al, U.S. Pat. No. 5,322,938.

A construct is a package of genetic material inserted into the genome of a cell via various techniques. The term nucleic acid construct refers to a coding sequence or sequences operably linked to appropriate regulatory sequences and inserted into a vector for transforming a cell. Such a nucleic acid construct may contain a coding sequence for a gene product of interest, along with a marker gene and/or a reporter gene.

A cassette refers to a segment of DNA that can be inserted into a vector at specific restriction sites. The segment of DNA encodes a polypeptide of interest or produces RNA, and the cassette and restriction sites are designed to ensure insertion of the cassette in the proper reading frame for transcription and translation.

A vector is a means for the transfer of a nucleic acid into a host cell. A vector may be a replicon to which another DNA segment may be attached so as to bring about the replication of the attached segment. A replicon is any genetic element (e.g., plasmid, phage, cosmid, chromosome, virus) that functions as an autonomous unit of DNA or RNA replication in vivo, i.e., capable of replication under its own control. Unless indicated otherwise, the term "vector" includes both viral and nonviral means for introducing the nucleic acid into a cell in vitro, ex vivo or in vivo.

In an example, the nucleic acid molecule may be expressed by a recombinant vector, viral vector, or virus. As described more fully below, in a preferred embodiment the recombinant virus vectors include adenovirus and alphavirus vectors. In another example, Venezuelan equine encephalitis (VEE) vectors such as strains V3526 or TC-83 are employed. The techniques employed to insert such a sequence into the viral vector and make ether alterations in the viral DNA, e.g., to insert linker sequences and the like, are known to one of skill in the art. (See, e.g., Sambrook et al, Molecular Cloning: A Laboratory Manual, Third editions, Cold Spring Harbor Laboratory, Cold Spring Harbor, N.Y. 2001.

In one embodiment the vaccine is produced using an alphavirus vector (referred to in some instances as RNA particle or RP) technology. RP are produced by introducing into cell in culture a replicon RNA that expresses the foreign gene and two helper RNAs, one that codes for the alphavirus capsid protein and the other that codes for the alphavirus glycoproteins (E2 and E1). These RNAs can be introduced into cells using a number of methods such as lipid transfection or electroporation. After the three RNAs have been introduced into cells the replicon RNA replicates itself in-cis and the helper RNAs in-trans. The helper RNAs produce the structural proteins which recognize the replicon RNA and package it into RP. RP expressing the foreign gene constitutes the autogenous vaccine. The methods and variations of same used to produce such replicons are known to one skilled in the art. Illustrative methodology can be found at U.S. Pat. No. 6,156,558, incorporated herein by reference in its entirety, and also at U.S. Pat. Nos. 6,521,235; 6,531,135; and 7,442,381; 6,541,010; 7,045,335; and 5,792,462 all of which are incorporated herein by reference in their entirety.

Alphavirus vectors and alphavirus replicon particles are used in embodiments of the invention. The term "alphavirus" has its conventional meaning in the art and includes the various species of alphaviruses which are members of the Togaviridae family. This includes alphaviruses such as Eastern Equine Encephalitis virus (EEE), Venezuelan Equine Encephalitis virus (VEE), Everglades virus, Mucambo virus, Pixuna virus, Western Equine Encephalitis virus (WEE), Sindbis virus, South African Arbovirus No. 86, Semliki Forest virus, Middelburg virus, Chikungunya virus, O'nyong-nyong virus, Ross River virus, Barmah Forest virus, Getah virus, Sagiyama virus, Bebaru virus, Mayaro virus, Una virus, Aura virus, Whataroa virus, Babanki virus, Kyzylagach virus, Highlands J virus, Fort Morgan virus, Ndumu virus, and Buggy Creek virus. The viral genome is a single-stranded, messenger-sense RNA, modified at the 5'-end with a methylated cap, and at the 3'-end with a variable-length poly (A) tract. Structural subunits containing a single viral protein, C, associate with the RNA genome in an icosahedral nucleocapsid. In the virion, the capsid is surrounded by a lipid envelope covered with a regular array of transmembrane protein spikes, each of which consists of a heterodimeric complex of two glycoproteins, E1 and E2. See Pedersen et al., J. Virol. 14:40 (1974). The Sindbis and Semliki Forest viruses are considered the prototypical alphaviruses and have been studied extensively. See Schlesinger The Togaviridae and Flaviviridae, Plenum Publishing Corp., New York (1986). The VEE virus has also been studied. See U.S. Pat. No. 5,185,440 to Davis et al.

As the above patents illustrate, use of alphavirus replicon particles to produce protective molecules are processes known to one skilled in the art. There are many modifications to the process available, and any process using a replicon subunit or replicon particle methodology can be used with the invention. Thus the system in one embodiment provides for infectious, defective, alphavirus particles, wherein each particle comprises an alphavirus replicon RNA, and wherein the replicon RNA comprises an alphavirus packaging signal, one or more heterologous RNA sequence(s), and a sequence encoding at least one alphavirus structural protein, and wherein the replicon RNA furthermore lacks a sequence encoding at least one alphavirus structural protein; wherein the population contains no detectable replication-competent alphavirus particles as determined by passage on permissive cells in culture. For example, in U.S. Pat. No. 6,531,135, incorporated herein by reference in its entirety is shown in an embodiment an RP system which uses a helper cell for expressing an infectious, replication defective, alphavirus particle in an alphavirus-permissive cell. The helper cell includes (a) a first helper RNA encoding (i) at least one alphavirus structural protein, and (ii) not encoding at least one alphavirus structural protein; and (b) a second helper RNA separate from the first helper RNA, the second helper RNA (i) not encoding at least one alphavirus structural protein encoded by the first helper RNA, and (ii) encoding at least one alphavirus structural protein not encoded by the first helper RNA, such that all of the alphavirus structural proteins assemble together into alphavirus particles in the cell. Preferably, the alphavirus packaging segment is deleted from at least the first helper RNA.

There are many variations that are available to one skilled in the art when preparing such replicons. For example, in another embodiment, the helper cell also includes a replicon RNA, which encodes the alphavirus packaging segment and an inserted heterologous RNA. In the embodiment wherein the helper cell also includes a replicon RNA, the alphavirus packaging segment may be, and preferably is, deleted from both the first helper RNA and the second helper RNA. For example, in the embodiment wherein the helper cell includes a replicon RNA encoding the alphavirus packaging segment and an inserted heterologous RNA, the first helper RNA includes the alphavirus E1 glycoprotein and the alphavirus E2 glycoprotein, and the second helper RNA includes the alphavirus capsid protein. The replicon RNA, first helper RNA, and second helper RNA in an embodiment are all on separate molecules and are cotransfected into the host cell.

In an alternative embodiment, the helper cell includes a replicon RNA encoding the alphavirus packaging segment, an inserted heterologous RNA, and the alphavirus capsid protein encoded by the second helper RNA, and the first helper RNA includes the alphavirus E1 glycoprotein and the alphavirus E2 glycoprotein. Thus, the replicon RNA and the first helper RNA are on separate molecules, and the replicon RNA and the second helper RNA are on a single molecule. The heterologous RNA comprises a foreign RNA.

The RNA encoding the structural proteins, i.e., the first helper RNA and the second helper RNA, may advantageously include one or more attenuating mutations. In an embodiment, at least one of the first helper RNA and the second helper RNA includes at least one attenuating mutation. The attenuating mutations provide the advantage that in the event of RNA recombination within the cell, the coming together of the structural and nonstructural genes will produce a virus of decreased virulence.

In another aspect a method of making infectious, non-living replication defective, alphavirus particles are provided. The method includes transfecting a helper cell as given above with a replication defective replicon RNA, producing the alphavirus particles in the transfected cell, and then collecting the alphavirus particles from the cell. The replicon RNA encodes the alphavirus packaging segment and a heterologous RNA. The transfected cell further includes the first helper RNA and second helper RNA as described above.

In another aspect, a set of RNAs is provided for expressing an infectious, non-living replication defective alphavirus. The set of RNAs comprises, in combination, (a) a replicon RNA encoding a promoter sequence, an inserted heterologous RNA, wherein RNA encoding at least one structural protein of the alphavirus is deleted from the replicon RNA so that the replicon RNA is replication defective, and (b) a first helper RNA separate from the replicon RNA, wherein the first helper RNA encodes in trans, the structural protein which is deleted from the replicon RNA and which may or may not include a promoter sequence. In this embodiment, it is preferred that an RNA segment encoding at least one of the structural proteins is located on an RNA other than the first helper RNA. Thus, for example, the set of RNAs may include a replicon RNA including RNA which encodes the alphavirus packaging sequence, the inserted heterologous RNA, and the alphavirus capsid protein, but both the alphavirus E1 glycoprotein and alphavirus E2 glycoprotein are deleted therefrom; and a first helper RNA includes RNA encoding both the alphavirus E1 glycoprotein and the alphavirus E2 glycoprotein.

In another embodiment, the set of RNAs also includes a second helper RNA separate from the replicon RNA and the first helper RNA. In this embodiment, the second helper RNA encodes, in trans, at least one structural protein, which is different from the structural protein encoded by the replicon RNA and by the first helper RNA. Thus, for example, the set of RNAs may include a replicon RNA including RNA which encodes the alphavirus packaging sequence, and the inserted heterologous RNA; a first helper RNA including RNA which may encode a promoter sequence and an RNA encoding both the alphavirus E1 glycoprotein and the alphavirus E2 glycoprotein; and a second helper RNA including RNA which encodes the alphavirus capsid protein, with the replicon RNA, the first helper RNA, and the second helper RNA being in trans from each other, on separate molecules.

As another aspect, provided is a pharmaceutical formulation comprising infectious alphavirus particles as described above, in an effective immunogenic amount in a pharmaceutically acceptable carrier. See, for example, the '135 patent at column 2, line 10-column 11 line 52 which includes examples 1-5.

The phrases "structural protein" or "alphavirus structural protein" as used herein refer to the encoded proteins which are required for production of particles that contain the replicon RNA, and include the capsid protein, E1 glycoprotein, and E2 glycoprotein. As described hereinabove, the structural proteins of the alphavirus are distributed among one or more helper RNAs (i.e., a first helper RNA and a second helper RNA). In addition, one or more structural proteins may be located on the same RNA molecule as the replicon RNA, provided that at least one structural protein is deleted from the replicon RNA such that the replicon and resulting alphavirus particle are replication defective. As used herein, the terms "deleted" or "deletion" mean either total deletion of the specified segment or the deletion of a sufficient portion of the specified segment to render the segment inoperative or nonfunctional, in accordance with standard usage. See, e.g., U.S. Pat. No. 4,650,764 to Temin et al. The term "replication defective" as used herein, means that the replicon RNA cannot produce particles in the host cell in the absence of the helper RNA. That is, no additional particles can be produced in the host cell. The replicon RNA is replication defective inasmuch as the replicon RNA does not include all of the alphavirus structural proteins required for production of particles because at least one of the required structural proteins has been deleted therefrom.

The helper cell for production of the infectious, replication defective, alphavirus particle comprises a set of RNAs, as described above. The set of RNAs principally include a first helper RNA and a second helper RNA. The first helper RNA includes RNA encoding at least one alphavirus structural protein but does not encode all alphavirus structural proteins. In other words, the first helper RNA does not encode at least one alphavirus structural protein; that is, at least one alphavirus structural protein gene has been deleted from the first helper RNA. In one embodiment, the first helper RNA includes RNA encoding the alphavirus E1 glycoprotein, with the alphavirus capsid protein and the alphavirus E2 glycoprotein being deleted from the first helper RNA. In another embodiment, the first helper RNA includes RNA encoding the alphavirus E2 glycoprotein, with the alphavirus capsid protein and the alphavirus E1 glycoprotein being deleted from the first helper RNA. In a third, preferred embodiment, the first helper RNA includes RNA encoding the alphavirus E1 glycoprotein and the alphavirus E2 glycoprotein, with the alphavirus capsid protein being deleted from the first helper RNA.

The second helper RNA includes RNA encoding the capsid protein which is different from the structural proteins encoded by the first helper RNA. In the embodiment wherein the first helper RNA includes RNA encoding only the alphavirus E1 glycoprotein, the second helper RNA may include RNA encoding one or both of the alphavirus capsid protein and the alphavirus E2 glycoprotein which are deleted from the first helper RNA. In the embodiment wherein, the first helper RNA includes RNA encoding only the alphavirus E2 glycoprotein, the second helper RNA may include RNA encoding one or both of the alphavirus capsid protein and the alphavirus E1 glycoprotein which are deleted from the first helper RNA. In the embodiment wherein the first helper RNA includes RNA encoding both the alphavirus E1 glycoprotein and the alphavirus E2 glycoprotein, the second helper RNA may include RNA encoding the alphavirus capsid protein which is deleted from the first helper RNA.

In one embodiment, the packaging segment or "encapsidation sequence" is deleted from at least the first helper RNA. In a preferred embodiment, the packaging segment is deleted from both the first helper RNA and the second helper RNA.

In an embodiment wherein the packaging segment is deleted from both the first helper RNA and the second helper RNA, preferably the helper cell contains a replicon RNA in addition to the first helper RNA and the second helper RNA. The replicon RNA encodes the packaging segment and an inserted heterologous RNA. The inserted heterologous RNA may be RNA encoding a protein or a peptide. The inserted heterologous RNA may encode a protein or a peptide which is desirously expressed by the host, alphavirus-permissive cell, and includes the promoter and regulatory segments necessary for the expression of that protein or peptide in that cell.

For example, in one embodiment, the helper cell includes a set of RNAs which include (a) a replicon RNA including RNA encoding an alphavirus packaging sequence and an inserted heterologous RNA, (b) a first helper RNA including RNA encoding the alphavirus E1 glycoprotein and the alphavirus E2 glycoprotein, and (c) a second helper RNA including RNA encoding the alphavirus capsid protein so that the alphavirus E1 glycoprotein, the alphavirus E2 glycoprotein and the capsid protein assemble together into alphavirus particles in the host cell.

In an alternate embodiment, the replicon RNA and the first helper RNA are on separate molecules, and the replicon RNA and the second helper RNA are on a single molecule together, such that a first molecule, i.e., the first helper RNA, including RNA encoding at least one but not all of the required alphavirus structural proteins, and a second molecule, i.e., the replicon RNA and second helper RNA, including RNA encoding the packaging segment, the inserted heterologous DNA and the capsid protein. Thus, the capsid protein is encoded by the second helper RNA, but the second helper RNA is located on the second-molecule together with the replicon RNA. For example, in one preferred embodiment of the present invention, the helper cell includes a set of RNAs including (a) a replicon RNA including RNA encoding an alphavirus packaging sequence, an inserted heterologous RNA, and an alphavirus capsid protein, and (b) a first helper RNA including RNA encoding the alphavirus E1 glycoprotein and the alphavirus E2 glycoprotein so that the alphavirus E1 glycoprotein, the alphavirus E2 glycoprotein and the capsid protein assemble together into alphavirus particles in the host cell.

In one embodiment, the RNA encoding the alphavirus structural proteins, i.e., the capsid, E1 glycoprotein and E2 glycoprotein, contains at least one attenuating mutation. The phrases "attenuating mutation" and "attenuating amino acid," as used herein, mean a nucleotide mutation or an amino acid coded for in view of such a mutation which result in a decreased probability of causing disease in its host (i.e., a loss of virulence), in accordance with standard terminology in the art, See, e.g., B. Davis, et al., Microbiology 132 (3d ed. 1980), whether the mutation be a substitution mutation or an in-frame deletion mutation. The phrase "attenuating mutation" excludes mutations which would be lethal to the virus. Thus, according to this embodiment, at least one of the first helper RNA and the second helper RNA includes at least one attenuating mutation. In a more preferred embodiment, at least one of the first helper RNA and the second helper RNA includes at least two, or multiple, attenuating mutations. The multiple attenuating mutations may be positioned in either the first helper RNA or in the second helper RNA, or they may be distributed randomly with one or more attenuating mutations being positioned in the first helper RNA and one or more attenuating mutations positioned in the second helper RNA. Appropriate attenuating mutations will be dependent upon the alphavirus used. For example, when the alphavirus is VEE, suitable attenuating mutations may be selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threonine as E1 amino acid 253.

In an alternate embodiment, wherein the alphavirus is the South African Arbovirus No. 86 (S.A.AR86), suitable attenuating mutations may be selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372. Suitable attenuating mutations useful in embodiments wherein other alphaviruses are employed are known to those skilled in the art. Attenuating mutations may be introduced into the RNA by performing site-directed mutagenesis on the cDNA which encodes the RNA, in accordance with known procedures. See, Kunkel, Proc. Natl. Acad. Sci. USA 82:488 (1985). Alternatively, mutations may be introduced into the RNA by replacement of homologous restriction fragments in the cDNA which encodes for the RNA, in accordance with known procedures.

A synthetic plasmid vector is used called pVEK. The pVEK plasmid vectors incorporate derivatives of the nonstructural genes from the attenuated Venezuelan equine encephalitis VEE virus vaccine, TC-83. (See, for example U.S. Pat. No. 9,079,943, incorporated herein by reference in its entirety.) The pVEK plasmid vectors have been modified for optimal donor gene expression (Kamrud, K. I., Custer, M., Dudek, J. M., Owens, G., Alterson, K. D., Lee, J. S., Groebner, J. L. & Smith, J. F. (2007). Alphavirus replicon approach to promoterless analysis of IRES elements. Virology. 360, 376-87. Epub 2006 Dec. 6.). The plasmids are linearized and RNA is transcribed from the plasmid DNA with T7 Express enzyme in the presence of Cap analog (Promega, Madison, Wis.) and purified. The purified RNA is electroporated into Vero cells (derived from Master Cells) for translation into autogenous recombinant proteins. Neither the pVEK plasmid vector nor the transcribed RNA contain the structural, capsid, or glycoprotein genes for TC-83.

The nonstructural genes aid in the expression of the autogenous recombinant proteins by forming a complex which transcribes additional autogenous recombinant gene RNA. Nsp1 serves as the capping enzyme and is believed to play a major role in the binding and assembly of the complex. Nsp2 is an RNA binding protein that has NTPase activity and likely functions as a RNA helicase to unwind duplex RNA. Nsp2 also functions as a protease that is required for post-translational processing of the nonstructural polyproteins. Nsp3 is a phosphoprotein whose role has not been determined. Nsp4 has been identified as the RNA polymerase. Rayner, et al. (2002). Alphavirus vectors and vaccination. *Rev Med Virol* 12, 279-96.

The pVEK vectors control protein expression at the level of translation by incorporating internal ribosome entry site (IRES) elements associated with each donor gene (Kamrud, et al. (2007). Alphavirus replicon approach to promoterless analysis of IRES elements. *Virology.* 360, 376-87. Epub 2006 Dec. 6.). The sequence differs from the TC-83 genomic sequence by four mutations and the absence of all TC-83 structural genes. In addition, a kanamycin resistance Open Reading Frame has been inserted into the plasmid backbone as a selective marker to amplify *E. coli* that contain the replicon plasmid DNA. A multiple cloning site has also been inserted in place of the structural protein genes. The resulting plasmid, pVEK, is replicated in bacteria using the COLE1 origin of replication and contains a 5' untranslated region, TC-83 nonstructural protein sequences, a 26S promoter, a multiple cloning site and a 3' untranslated region, all placed downstream of a T7 polymerase promoter for in vitro RNA transcription.

As with alphavirus vectors, an adenoviral vector is a replication deficient virus vector that can express a nucleic acid molecule. They have been used to express a variety of nucleic acid molecules. Examples of adenovirus vectors and their production are discussed, for example, where used to produce a vaccine expressing a sequence of the Dengue virus, see U.S. Pat. No. 8,920,813; or a human CFTR protein, see U.S. Pat. No. 6,136,594, each of which are incorporated herein by reference in their entirety. There are many variations on specific components and processes of producing a replication deficient adenovirus vector, and the following is provided by way of example and not limitation.

Adenovirus from various origins, subtypes, or mixture of subtypes can be used as the source of the viral genome for the adenoviral vector. Non-human adenovirus (e.g., simian, avian, canine, ovine, or bovine adenoviruses) can be used to generate the adenoviral vector. For example, the adenoviral vector can be based on a simian adenovirus, including both new world and old world monkeys (see, e.g., Virus Taxonomy: VIIIth Report of the International Committee on Taxonomy of Viruses (2005)). The phylogeny of adenoviruses that infect primates is disclosed in, e.g., Roy et al., *PLoS Pathog.,* 5(7): e100050. doi:10.1371/journal.ppat.1000503 (2009). For instance, a simian adenovirus can be of serotype 1, 3, 6, 7, 11, 16, 18, 19, 20, 27, 33, 38, 39, 48, 49, or 50, or any other simian adenoviral serotype. Other non-human adenoviruses which can be used in the invention include non-human primate adenoviruses that are genetically and/or phenotypically similar to group C human adenoviruses. A human adenovirus can be used as the source of the viral genome for the adenoviral vector. For instance, an adenovirus can be of subgroup A (e.g., serotypes 12, 18, and 31), subgroup B (e.g., serotypes 3, 7, 11, 14, 16, 21, 34, 35, and 50), subgroup C (e.g., serotypes 1, 2, 5, and 6), subgroup D (e.g., serotypes 8, 9, 10, 13, 15, 17, 19, 20, 22-30, 32, 33, 36-39, and 42-48), subgroup E (e.g., serotype 4), subgroup F (e.g., serotypes 40 and 41), an unclassified serogroup (e.g., serotypes 49 and 51), or any other adenoviral serotype. Adenoviral serotypes 1 through 51 (i.e., Ad1 through Ad51) are available from the American Type Culture Collection (ATCC, Manassas, Va.). In an embodiment, the adenoviral vector is of human subgroup C, especially serotype 2 or even more desirably serotype 5. However, non-group C adenoviruses can be used to prepare adenoviral gene transfer vectors for delivery of gene products to host cells. Examples of adenoviruses used in the construction of non-group C adenoviral gene transfer vectors include Ad12 (group A), Ad7 and Ad35 (group B), Ad30 and Ad36 (group D), Ad4 (group E), and Ad41 (group F). Non-group C adenoviral vectors, methods of producing non-group C adenoviral vectors, and methods of using non-group C adenoviral vectors are disclosed in, for example, U.S. Pat. Nos. 5,801,030, 5,837,511, and 5,849,561, and International Patent Application Publications WO 1997/012986 and WO 1998/053087.

The '813 patent describes variations on preparation of adenovirus vectors, such as where the adenoviral vector can comprise portions of an adenoviral genome of two or more (e.g., a mixture of) subtypes, in addition to containing a nucleic acid sequence encoding the chimeric hexon protein as described herein, and thereby be a "chimeric" adenoviral vector. A chimeric adenoviral vector can comprise an adenoviral genome that is derived from two or more (e.g., 2, 3, 4, etc.) different adenovirus serotypes. In one version, a chimeric adenoviral vector can comprise approximately different or equal amounts of the genome of each of the two or more different adenovirus serotypes.

In an embodiment, the adenoviral vector is replication-deficient, such that the replication-deficient adenoviral vector requires complementation of at least one replication-essential gene function of one or more regions of the adenoviral genome for propagation (e.g., to form adenoviral vector particles). A replication-deficient adenoviral vector is an adenoviral vector that requires complementation of one or more gene functions or regions of the adenoviral genome that are required for replication, as a result of, for example, a deficiency in one or more replication-essential gene function or regions, such that the adenoviral vector does not replicate in typical host cells, especially those in a human to be infected by the adenoviral vector.

A deficiency in a gene function or genomic region, can be a disruption (e.g., deletion) of sufficient genetic material of the adenoviral genome to obliterate or impair the function of the gene (e.g., such that the function of the gene product is reduced by at least about 2-fold, 5-fold, 10-fold, 20-fold, 30-fold, or 50-fold) whose nucleic acid sequence was disrupted (e.g., deleted) in whole or in part. Deletion of an entire gene region often is not required for disruption of a replication-essential gene function. However, for the purpose of providing sufficient space in the adenoviral genome for one or more transgenes, removal of a majority of one or more gene regions may be desirable. While deletion of genetic material is preferred, mutation of genetic material by addition or substitution also is appropriate for disrupting gene function. Replication-essential gene functions are those gene functions that are required for adenovirus replication (e.g., propagation) and are encoded by, for example, the adenoviral early regions (e.g., the E1, E2, and E4 regions), late regions (e.g., the L1, L2, L3, L4, and L5 regions), genes involved in viral packaging (e.g., the IVa2 gene), and virus-associated RNAs (e.g., VA-RNA-1 and/or VA-RNA-2).

The replication-deficient adenoviral vector can be modified in any suitable manner to cause the deficiencies in the one or more replication-essential gene functions in one or more regions of the adenoviral genome for propagation. The complementation of the deficiencies in the one or more replication-essential gene functions of one or more regions of the adenoviral genome can refer to the use of exogenous means to provide the deficient replication-essential gene functions. Such complementation can be effected in any suitable manner, for example, by using complementing cells and/or exogenous DNA (e.g., helper adenovirus) encoding the disrupted replication-essential gene functions.

The adenoviral vector can be deficient in one or more replication-essential gene functions of only the early regions (i.e., E1-E4 regions) of the adenoviral genome, only the late regions (i.e., L1-L5 regions) of the adenoviral genome, both the early and late regions of the adenoviral genome, or all adenoviral genes (i.e., a high capacity adenovector (HC-Ad). See Morsy et al., Proc. Natl. Acad. Sci. USA, 95: 965-976 (1998); Chen et al., Proc. Natl. Acad. Sci. USA, 94: 1645-1650 (1997); and Kochanek et al., Hum. Gene Ther., 10: 2451-2459 (1999). Examples of replication-deficient adenoviral vectors are disclosed in U.S. Pat. Nos. 5,837,511; 5,851,806; 5,994,106; 6,127,175; 6,482,616; and 7,195,896, and International Patent Application Publications WO 1994/028152, WO 1995/002697, WO 1995/016772, WO 1995/034671, WO 1996/022378, WO 1997/012986, WO 1997/021826, and WO 2003/022311.

The early regions of the adenoviral genome include the E1, E2, E3, and E4 regions. The E1 region comprises the E1A and E1B subregions, and one or more deficiencies in replication-essential gene functions in the E1 region can include one or more deficiencies in replication-essential gene functions in either or both of the E1A and E1B subregions, thereby requiring complementation of the E1A subregion and/or the E1B subregion of the adenoviral genome for the adenoviral vector to propagate (e.g., to foam adenoviral vector particles). The E2 region comprises the E2A and E2B subregions, and one or more deficiencies in replication-essential gene functions in the E2 region can include one or more deficiencies in replication-essential gene functions in either or both of the E2A and E2B subregions, thereby requiring complementation of the E2A subregion and/or the E2B subregion of the adenoviral genome for the adenoviral vector to propagate (e.g., to form adenoviral vector particles).

The E3 region does not include any replication-essential gene functions, such that a deletion of the E3 region in part or in whole does not require complementation of any gene functions in the E3 region for the adenoviral vector to propagate (e.g., to form adenoviral vector particles). In the context of the invention, the E3 region is defined as the region that initiates with the open reading frame of the 12.5K protein from the E3 region of human adenovirus 5 (NCBI reference sequence AP_000218) and ends with the open reading frame that encodes the 14.7K protein from the E3 region of human adenovirus 5 (NCBI reference sequence AP_000224.1). The E3 region may be deleted in whole or in part or retained in whole or in part. The size of the deletion may be tailored so as to retain an adenoviral vector whose genome closely matches the optimum genome packaging size. A larger deletion will accommodate the insertion of larger heterologous nucleic acid sequences in the adenoviral genome.

The E4 region comprises multiple open reading frames (ORFs). An adenoviral vector with a deletion of all of the open reading frames of the E4 region except ORF6, and in some cases ORF3, does not require complementation of any gene functions in the E4 region for the adenoviral vector to propagate (e.g., to form adenoviral vector particles). Conversely, an adenoviral vector with a disruption or deletion of ORF6, and in some cases ORF3, of the E4 region (e.g., with a deficiency in a replication-essential gene function based in ORF6 and/or ORF3 of the E4 region), with or without a disruption or deletion of any of the other open reading frames of the E4 region or the native E4 promoter, polyadenylation sequence, and/or the right-side inverted terminal repeat (ITR), requires complementation of the E4 region (specifically, of ORF6 and/or ORF3 of the E4 region) for the adenoviral vector to propagate (e.g., to form adenoviral vector particles). The late regions of the adenoviral genome include the L1, L2, L3, L4, and L5 regions. The adenoviral vector also can have a mutation in the major late promoter (MLP), as discussed in International Patent Application Publication WO 2000/000628, which can render the adenoviral vector replication-deficient if desired.

The one or more regions of the adenoviral genome that contain one or more deficiencies in replication-essential gene functions desirably are one or more early regions of the adenoviral genome, i.e., the E1, E2, and/or E4 regions, optionally with the deletion in part or in whole of the E3 region.

The replication-deficient adenoviral vector also can have one or more mutations as compared to the wild-type adenovirus (e.g., one or more deletions, insertions, and/or substitutions) in the adenoviral genome that do not inhibit viral replication in host cells. Thus, in addition to one or more deficiencies in replication-essential gene functions, the adenoviral vector can be deficient in other respects that are not replication-essential. For example, the adenoviral vector can have a partial or entire deletion of the adenoviral early region known as the E3 region, which is not essential for propagation of the adenoviral genome.

In one embodiment, the adenoviral vector is replication-deficient and requires, at most, complementation of the E1 region or the E4 region of the adenoviral genome, for propagation (e.g., to form adenoviral vector particles). Thus, the replication-deficient adenoviral vector requires complementation of at least one replication-essential gene function of the E1A subregion and/or the E1B region of the adenoviral genome (denoted an E1-deficient adenoviral vector) or the E4 region of the adenoviral genome (denoted an E4-deficient adenoviral vector) for propagation (e.g., to form adenoviral vector particles). The adenoviral vector can be deficient in at least one replication-essential gene function (desirably all replication-essential gene functions) of the E1 region of the adenoviral genome and at least one gene function of the nonessential E3 region of the adenoviral genome (denoted an E1/E3-deficient adenoviral vector). The adenoviral vector can be deficient in at least one replication-essential gene function (desirably all replication-essential gene functions) of the E4 region of the adenoviral genome and at least one gene function of the nonessential E3 region of the adenoviral genome (denoted an E3/E4-deficient adenoviral vector).

In one embodiment, the adenoviral vector is replication-deficient and requires, at most, complementation of the E2 region, preferably the E2A subregion, of the adenoviral genome, for propagation (e.g., to form adenoviral vector particles). Thus, the replication-deficient adenoviral vector requires complementation of at least one replication-essential gene function of the E2A subregion of the adenoviral genome (denoted an E2A-deficient adenoviral vector) for propagation (e.g., to form adenoviral vector particles). The adenoviral vector can be deficient in at least one replication-essential gene function (desirably all replication-essential gene functions) of the E2A region of the adenoviral genome and at least one gene function of the nonessential E3 region of the adenoviral genome (denoted an E2A/E3-deficient adenoviral vector).

In one embodiment, the adenoviral vector is replication-deficient and requires, at most, complementation of the E1 and E4 regions of the adenoviral genome for propagation (e.g., to form adenoviral vector particles). Thus, the replication-deficient adenoviral vector requires complementation of at least one replication-essential gene function of both the E1 and E4 regions of the adenoviral genome (denoted an E1/E4-deficient adenoviral vector) for propagation (e.g., to form adenoviral vector particles). The adenoviral vector can be deficient in at least one replication-essential gene function (desirably all replication-essential gene functions) of the E1 region of the adenoviral genome, at least one replication-essential gene function of the E4 region of the adenoviral genome, and at least one gene function of the nonessential E3 region of the adenoviral genome (denoted an E1/E3/E4-deficient adenoviral vector). The adenoviral vector in an embodiment requires, at most, complementation of the E1 region of the adenoviral genome for propagation and does not require complementation of any other deficiency of the adenoviral genome for propagation. The adenoviral vector can in another embodiment require, at most, complementation of the E1 and E4 regions of the adenoviral genome for propagation and does not require complementation of any other deficiency of the adenoviral genome for propagation.

The adenoviral vector, when deficient in multiple replication-essential gene functions of the adenoviral genome (e.g., an E1/E4-deficient adenoviral vector), can include a spacer sequence to provide viral growth in a complementing cell line similar to that achieved by adenoviral vectors deficient in a single replication-essential gene function (e.g., an E1-deficient adenoviral vector). The spacer sequence can contain any nucleotide sequence or sequences which are of a desired length, such as sequences at least about 15 base pairs (e.g., between about 15 nucleotides and about 12,000 nucleotides), preferably about 100 nucleotides to about 10,000 nucleotides, more preferably about 500 nucleotides to about 8,000 nucleotides, even more preferably about 1,500 nucleotides to about 6,000 nucleotides, and most preferably about 2,000 to about 3,000 nucleotides in length, or a range defined by any two of the foregoing values. The spacer sequence can be coding or non-coding and native or non-native with respect to the adenoviral genome but does not restore the replication-essential function to the deficient region. The spacer also can contain an expression cassette. More preferably, the spacer comprises a polyadenylation sequence and/or a gene that is non-native with respect to the adenoviral vector. The use of a spacer in an adenoviral vector is further described in, for example, U.S. Pat. No. 5,851,806 and International Patent Application Publication WO 1997/021826.

By removing all or part of the adenoviral genome, for example, the E1, E3, and E4 regions of the adenoviral genome, the resulting adenoviral vector is able to accept inserts of heterologous nucleic acid sequences while retaining the ability to be packaged into adenoviral capsids. A heterologous nucleic acid sequence can be inserted at any position in the adenoviral genome so long as insertion in the position allows for the formation of the adenoviral vector particle. The heterologous nucleic acid sequence preferably is positioned in the E1 region, the E3 region, or the E4 region of the adenoviral genome.

The replication-deficient adenoviral vector can be produced in complementing cell lines that provide gene functions not present in the replication-deficient adenoviral vector, but required for viral propagation, at appropriate levels in order to generate high titers of viral vector stock. Such complementing cell lines are known and include, but are not limited to, 293 cells (described in, e.g., Graham et al., J. Gen. Virol., 36: 59-72 (1977)), PER.C6 cells (described in, e.g., International Patent Application Publication WO 1997/000326, and U.S. Pat. Nos. 5,994,128 and 6,033,908), and 293-ORF6 cells (described in, e.g., International Patent Application Publication WO 1995/034671 and Brough et al., J. Virol., 71: 9206-9213 (1997)). Other suitable complementing cell lines to produce the replication-deficient adenoviral vector of the invention include complementing cells that have been generated to propagate adenoviral vectors encoding transgenes whose expression inhibits viral growth in host cells (see, e.g., U.S. Patent Application Publication 2008/0233650). Additional suitable complementing cells are described in, for example, U.S. Pat. Nos. 6,677,156 and 6,682,929, and International Patent Application Publication WO 2003/020879. In some instances, the cellular genome need not comprise nucleic acid sequences, the gene products of which complement for all of the deficiencies of a replication-deficient adenoviral vector. One or more replication-essential gene functions lacking in a replication-deficient adenoviral vector can be supplied by a helper virus, e.g., an adenoviral vector that supplies in trans one or more essential gene functions required for replication of the replication-deficient adenoviral vector. Alternatively, the inventive adenoviral vector can comprise a non-native replication-essential gene that complements for the one or more replication-essential gene functions lacking in the inventive replication-deficient adenoviral vector. For example, an E1/E4-deficient adenoviral vector can be engineered to contain a nucleic acid sequence encoding E4 ORF 6 that is obtained or derived from a different adenovirus (e.g., an adenovirus of a different serotype than the inventive adenoviral vector, or an adenovirus of a different species than the inventive adenoviral vector).

As can been seen, there are a variety of means of producing and variations to adenovirus and alphavirus vectors and their use available to one skilled in the art.

The vaccine can be administered as described herein to an animal. The method of the present invention is useful in animals including, but not limited to, humans, canine (e.g., dogs), feline (e.g., cats); equine (e.g., horses), bovine (e.g., cattle), and other animals which can develop cancer.

The vaccine may be administered prior to tumor development, upon diagnosis of cancer, where there is a recurrence of cancer after treatment of the cancer, and where other therapies have been employed. The methods and vaccines here are particularly useful with treating prostate cancer and is in an embodiment particularly useful where there has been prior treatment, such as surgery or radiation, but the cancer has recurred.

As used herein, the term "vaccine" as used herein refers to a pharmaceutical composition comprising at least one molecule, nucleic acid or polypeptide or fragment thereof that induces a protective response in an animal and possibly, but not necessarily, one or more additional components that enhance the activity of the active component. A vaccine may additionally comprise further components typical to pharmaceutical compositions. A vaccine may comprise one or simultaneously more than one of the elements described above.

The vaccine composition may be introduced into an animal, with a physiologically acceptable vehicle and/or adjuvant. Useful vehicles are well known in the art, and include, e.g., water, buffered water, saline, glycine, hyaluronic acid and the like. The resulting aqueous solutions may be packaged for use as is, or lyophilized, the lyophilized preparation being rehydrated prior to administration, as mentioned above. The compositions may contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like. In an embodiment, the molecule is combined with a binder that assists in associating the molecule with feed, which is particularly useful for oral administration. Such a water resistant binding substance can be any substance having such properties. Examples include, without limitation, agarose or other sugar compounds, albumin, alginate or any similar composition. In an embodiment the immunization composition includes an adjuvant to further enhance immune response. Any convenient adjuvant may be used, and many are well known to one skilled in the art. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses. Immunostimulatory agents or adjuvants have been used for many years to improve the host immune responses to, for example, vaccines. Examples, without meant to be limiting, include, *E. coli*, lipopolysaccharides, aluminum hydroxide and aluminum phosphate (alum), saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. Desirable characteristics of ideal adjuvants may include: (1) lack of toxicity; (2) ability to stimulate a long-lasting immune response; (3) simplicity of manufacture and stability in long-term storage; (4) ability to elicit both cell mediated immunity (CMI) and humoral immune response (HIR) to antigens administered by various routes; (5) synergy with other adjuvants; (6) capability of selectively interacting with populations of antigen presenting cells (APC); (7) ability to specifically elicit appropriate T-cell helper 1 (TH 1) or TH 2 cell-specific immune responses; and (8) ability to selectively increase appropriate antibody isotype levels (for example, IgA) against antigens. An adjuvant used need not possess all these characteristics.

In another embodiment, the nucleic acid molecule be administered with other protective or desirable compounds which may be administered sequentially or progressively or alternately administered simultaneously in an admixture.

In referring to administration of the vaccine, the vaccine may be "administered" in any suitable manner, including but not limited to, parenterally, by injection subcutaneously or intramuscularly, into an organ or cavity of the subject, reverse gavage (rectally), and oral. The vaccine can be administered by any means which includes, but is not limited to, syringes, nebulizers, misters, needleless injection devices, or microprojectile bombardment gene guns (Biolistic bombardment), via a liposome delivery system, naked delivery system, electroporation, viruses, vectors, viral vectors, or an ingestible delivery system wherein the protective molecules are consumed, for example, in feed or water or in any other suitable manner.

As used herein, "effective amount" refers to an amount, which is effective in reducing, eliminating, treating, preventing or controlling the symptoms of the cancer. The quantity to be administered depends on the subject to be treated, including, for example, the capacity of the individual to mount a protective response. Under normal circumstances the vaccine volume injected varies from 0.1 ml to 0.15 ml. We used 0.125 ml. in our Phase I and Phase II clinical trials of the adenovirus vaccine.

The following is provided by way of exemplification and is not intended to limit the scope of the invention. All references referred to herein are incorporated herein by reference.

EXAMPLES

Example 1

Preclinical studies by the inventors demonstrated the ability of a replication-deficient adenovirus, transformed with the gene for human prostate specific antigen (PSA) to induce strong anti-PSA and hence, anti-prostate tumor immune responses [Elzey, B. D., et al., Immunization with type 5 adenovirus recombinant for a tumor antigen in combination with recombinant canarypox virus (ALVAC) cytokine gene delivery induces destruction of established prostate tumors. *Int J Cancer,* 2001. 94(6): p. 842-9.]. Immunized mice were able to destroy PSA-secreting mouse prostate cancer cells and the immune destruction was a function of antigen-specific CD8+ T cells. Id. Following a large number of additional experiments Phase I and Phase II clinical trials were carried out in prostate cancer patients. The former trial demonstrated the safety of the vaccine and also provided preliminary data indicating the induction of immune response in patients as well improved clinical parameters [Lubaroff, D. M., et al., Phase I clinical trial of an adenovirus/prostate-specific antigen vaccine for prostate cancer: safety and immunologic results. *Clin Cancer Res,* 2009. 15(23): p. 7375-80]. In a further Phase II trial it was confirmed that the majority of patients had both immunologic and clinical benefits following immunization with the adenovirus/PSA (AdPSA) vaccine. Lubaroff et al., An ongoing phase II trial of an adenovirus vaccine for prostate cancer. *Amer Assoc Cancer Res Annual Meeting,* 2012; Lubaroff, D. M., Prostate cancer vaccines in clinical trials. *Expert Rev Vaccines,* 2012. 11(7): p. 857-68. However, the results were not absolute. Not all of the patients responded to the vaccine and those that did respond did not always have a sustained response.

Example 2

Preparation of Vectors

Adenovirus vectors and alphavirus vectors comprising the human prostate specific antigen (PSA) were produced. The PSA nucleic acid molecule used here is that found at Lundwall "Characterization of the gene for prostate-specific antigen, a human glandular kallikrein." Biochem Biophys Res Comm 1989; 161:1151-9 EMBL Accession No. X14810 (SEQ ID NO: 1). In the experiments here, the alphavirus vector employed was TC-83. The PSA gene was cloned into the AscI/PacI sites of the pVEK (TC-83) replicon vector (Hooper et al., 2009, "Molecular Smallpox Vaccine Delivered by Alphavirus Replicons Elicits Protective Immunity in Mice and Non-Human Primates" *Vaccine* 13(13)) and an optimized construct was selected. (Kamrud et al. Alphavirus replicon approach to promoterless analysis of IRES elements. *Virology.* 2007 Apr. 10; 360(2):376-87. Epub 2006 Dec. 6. PubMed PMID: 17156813; PubMed Central PMCID: PMC1885372). The adenovirus/PSA vaccine was produced as follows: The PSA cDNA provided by Donald Tindall, Mayo Clinic, Rochester, Minn., was placed 3' to the CMV promoter in a shuttle vector containing Ad5 DNA. The sequence inserted was the pre-pro form of PSA described by Lundwall. The cDNA encodes for 262 amino acids with a predicted molecular weight of 28.8 kDa. The shuttle vector and E1a-E1b deletion mutant Ad5 DNA were transfected into HEK 293 cells, and recombination between the DNA species was allowed to occur. The amplification and purification of Ad/PSA was performed by the University of Iowa Gene Transfer Vector Core.

The alphavirus platform approach is designed to produce a vaccine containing the prostate specific antigen (PSA) gene. Briefly, the PSA gene is cloned into DNA plasmids using the same full-length DNA incorporated into the adenovirus for the AdPSA vaccine. The plasmids are transcribed, producing RNA. The RNA is purified and electroporated into Vero cells. Once in the cells, the RNA is translated resulting in Viral Replicon Particles (VRP), encapsulating the replicon PSA RNA, are then harvested for formulation into VRP/PSA vaccine.

Preparation of Mice

Male Balb/c mice, at least 8 weeks old are obtained from The Jackson Laboratories, Bar Harbor, Me. The mice are injected subcutaneously with the E6 clone of the mouse prostate cancer cell line RM11/PSA 24 hours prior to the initiation of the heterologous prime-boost vaccine protocol. All rules and regulations of animal care are followed to insure humane care of mice throughout the studies. Tumor growth is monitored twice weekly and measurements made using a vernier caliper.

Preparation of Vaccines

The AdPSA and VRP/PSA vaccines are obtained from the manufacturer and stocks stored at −80 C in small volume cryotubes. For the preparation of treatment vaccines, the stock is diluted in phosphate-buffered saline (PBS) to obtain the desired dose for injection. For the AdPSA the concentration is 1×10E9 pfu/ml so that an injection dose of 0.1 ml contains 1×10E8 pfu. For the VRP/PSA the concentration is 5×10E9 particles/ml in order to deliver 5×10E8 particles in 0.1 ml.

Vaccination Regimes

Prime/Boost Vaccinations

The following prime/boost protocol was used on mice, wherein adeno vector prostate specific antigen vaccine (AdPSA) or alphavirus vector PSA antigen vaccine (alphaPSA or VRP/PSA) was administered. The E6 tumor cells were injected subcutaneously on day 0 and the first vaccination was administered at day 1, the second vaccination at day 14.

TABLE 1

| Prime injection | Booster injection |
|---|---|
| AdPSA | alphaPSA |
| alphaPSA | AdPSA |
| alphaPSA | alphaPSA |
| AdPSA | AdPSA |

Control mice received vaccines carrying the DNA or RNA for indifferent antigen and did not generate anti-PSA immune responses.

Figure 2A:
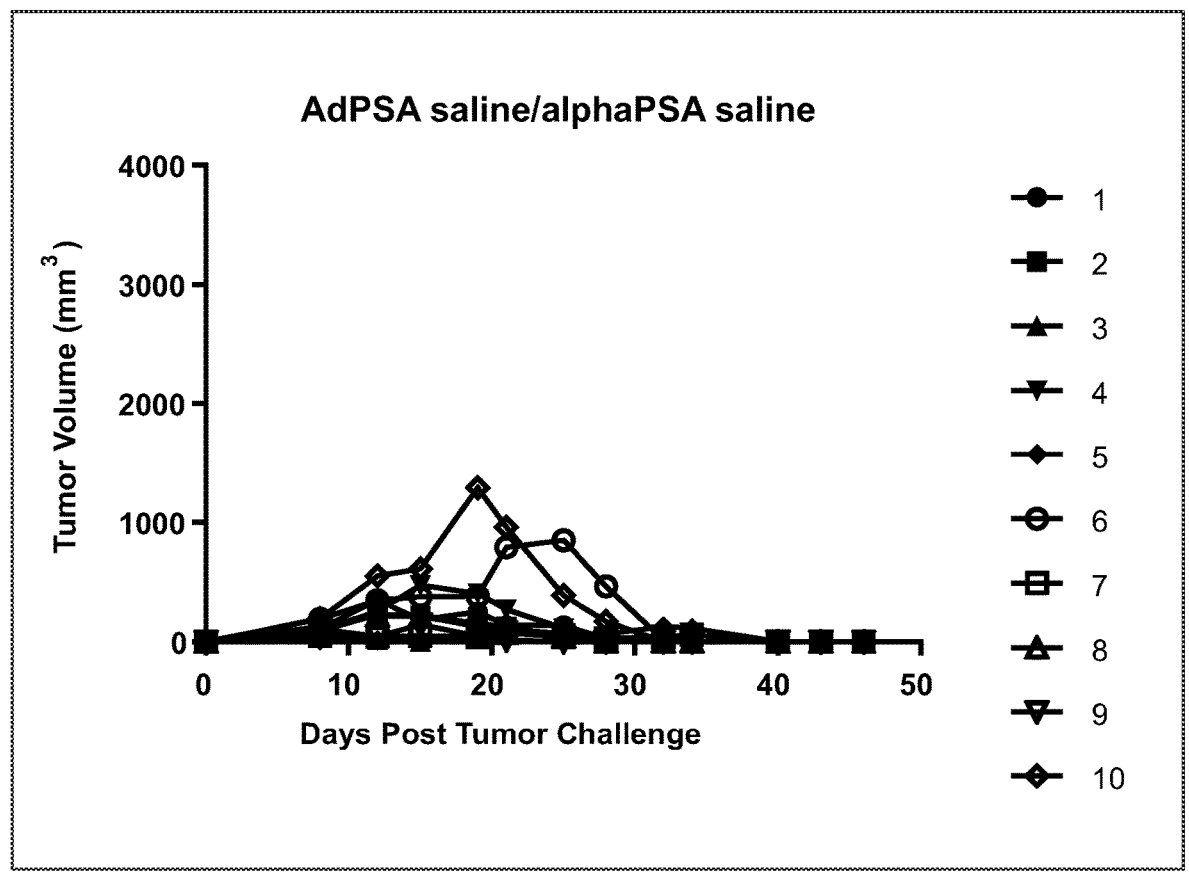
FIGS. 2A and 2B are graphs showing tumor volume (mm$^3$) and days post tumor challenges using the AdPSA saline/alphaPSA saline protocol (A) and alphaPSA saline/alphaPSA saline protocol (B).
Figure 2B:
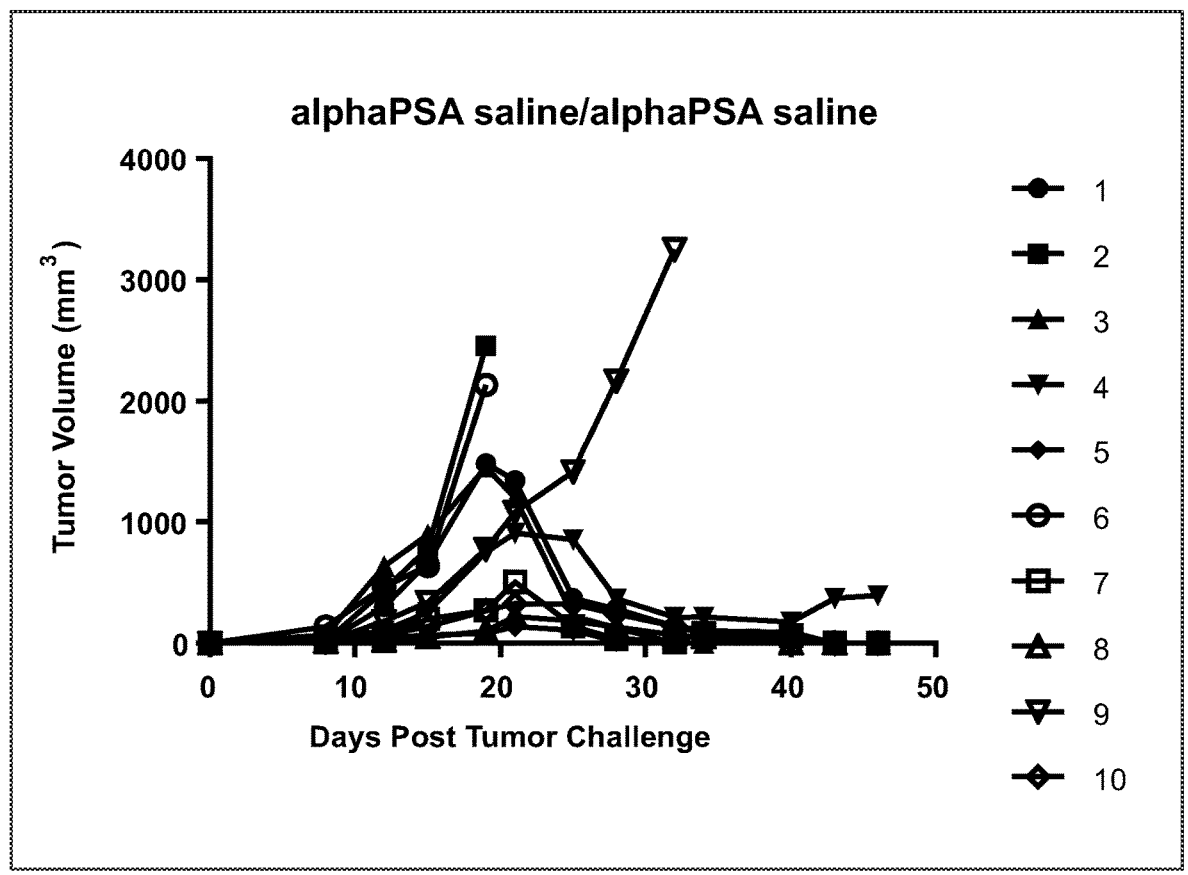
Figure 3:
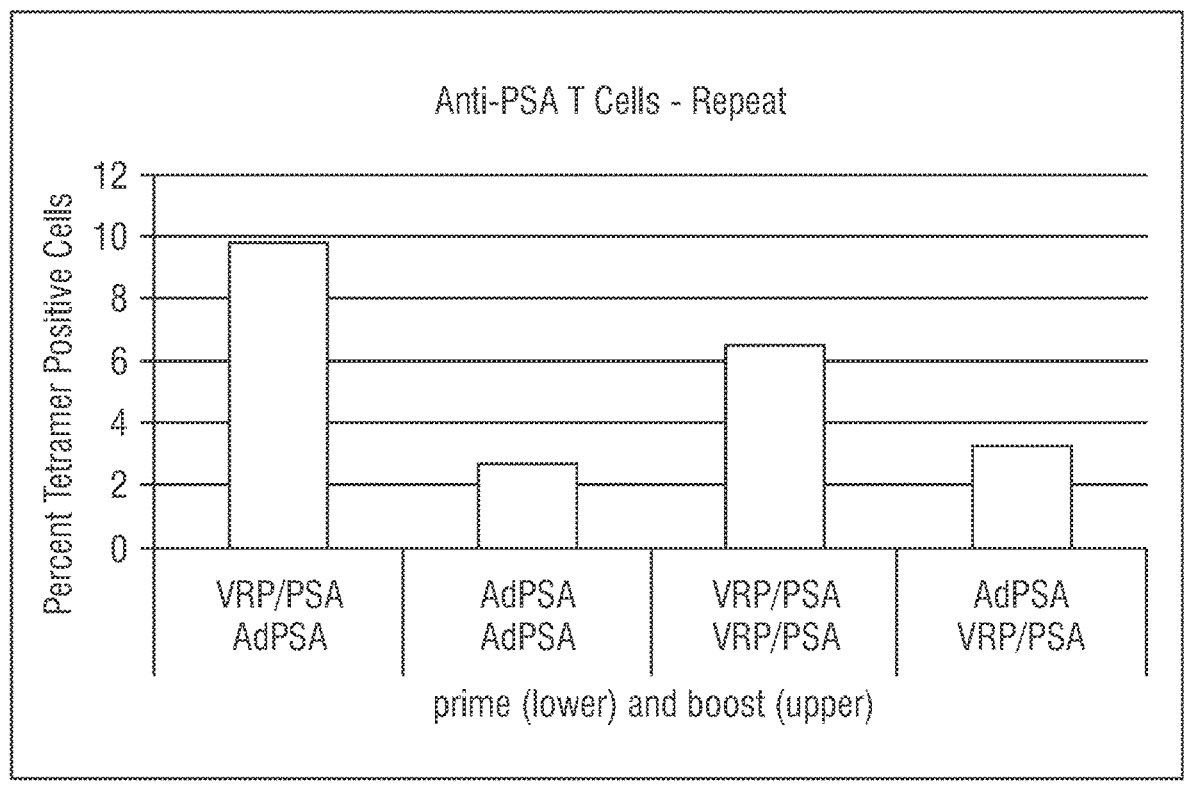
FIG. 3 is a graph showing the percent of tetramer positive cells resulting from differing vaccination administration as indicated.

The results, shown in FIGS. 1-3, demonstrated the superiority of using a priming injection of AdPSA with a booster injection of alphaPSA. The reverse combination or homologous combinations were not as effective in inducing anti-PSA immune responses.

Production of Anti PSA Tetramer Positive CD8+ T Cells Following Heterologous Prime-Boost Vaccination.

Mice were vaccinated with 1×10E8 AdPSA, 5×10E8 VRP/PSA, or controls of AdLacZ or VRP/GFP. Fourteen (14) days later the mice received booster vaccinations of either homologous or heterologous vaccines or controls.

Tetramer assays were run 7 days after the boost. The strongest responses were produced by an AdPSA prime followed by a VRP/PSA boost.

Complete Destruction of Established Tumors

Mice were injected subcutaneously with the E6 clone of RM11/PSA mouse prostate tumor cells, followed 24 hours later by a prime vaccination with AdPSA or VRP/PSA vaccine. All of the mice were boosted 14 days later with VRP/PSA vaccine as homologous or heterologous immunization. Tumor growth was monitored twice per week. The results (FIGS. 2A and 2B) demonstrate that, although the homologous vaccination of VRP/PSA (alphaPSA in figure)+VRP/PSA was effective in destroying tumors in 7/10 mice (70%), the heterologous vaccination of AdPSA+VRP/PSA resulted in the destruction of 10/10 (100%) mice. (In the graphs of FIGS. 2A and 2B, the numbers 1-10 represent separate mice.)

Example 4

Additional cancer protective nucleic acid molecule vaccines will be tested. These will be selected from, prostate stem cell antigen (PSCA), prostatic acid phosphatase (PAP), and prostate specific membrane antigen (PSMA) in addition to prostate specific antigen (PSA) These studies will identify the best method to induce the strongest antigen-specific immune responses and the destruction of mouse prostate tumor cells that express one or both antigens.

Example 5

Monovalent vaccines will contain RNA for a single antigen whereas a bivalent vaccine will contain the RNA for two different antigens, and trivalent vaccines will contain the RNA for three different antigens. Initial experiments will compare the efficacy of monovalent PSA and PSCA vaccines, bivalent PSA+PSCA vaccine, and a mixture of monovalent PSA and PSCA vaccines. Mice will be vaccinated with VRP/PSA, VRP/PSCA, VRP/PSA+PSCA, or a mixture of VRP/PSA and VRP/PSCA vaccines. We will perform dose escalation studies using 1×10E7, 5×10E7, 1×10E8, and 5×10E8 ffu with three vaccinations 14 days apart. Appropriate controls will be included. Seven days after the last vaccination blood will be analyzed for anti-PSA and anti-PSCA T cells and the mice injected with RM11/PSA and RM11/PSCA on opposite flanks. Tumor measurements and survival analysis will be performed as previously described.

Example 6

This experiment will use PAP and PSMA using the same protocols described above for PSA and PSCA. In addition to monovalent and bivalent studies trivalent vaccines in various combinations will be investigated.

Example 7

Immune responses to foreign antigens involve a large number of cells, receptors, ligands, cytokines, etc. which can have both positive and negative effects. The goal of cancer immunotherapy is to produce positive responses that result in the destruction of tumor antigen-expressing antigens. However, there are a number of factors that have a negative effect on the immune responses. These negative regulatory elements have been the target of investigators in attempts to induce the strongest and most effective anti-tumor immunity. Currently the most vigorously studied elements are the programmed cell death 1 (PD1) receptor and its ligand (PD-L1). The receptor is involved in down regulation of the immune system and referred to as an immune checkpoint that guards against autoimmunity. See for example Balar AV[1], Weber JS[2] PD-1 and PD-L1 antibodies in cancer: current status and future directions. *Cancer Immunol Immunother.* 2017 Feb. 17. 1954-6. [Epub ahead of print]. Antibodies to PD1 and PD-L1 have shown great promise as monotherapies for several cancers, but not all cancer patients respond. It now appears that the best responses are in patients that have some level of anti-tumor immunity. Our goal in these studies, both preclinical and clinical, is to combine the best vaccine immunotherapy with anti-PD1 or anti-PD-L1 antibody therapy. We predict that the establishment of anti-prostate tumor antigen(s) immune response will result in a high percentage of patients that will respond to checkpoint inhibitor therapies.

We will combine checkpoint inhibition therapy with the vaccine or vaccines that prove most efficacious by themselves in both preclinical and clinical studies. These may be monovalent VRP vaccines, bivalent VRP vaccines, trivalent VRP vaccines, or AdPSA-VRP/PSA prime-boost. Preclinical studies will be followed by clinical trials.

Example 8

The above experiment was repeated and FIG. 3 shows further verification of the prime:boost strategy outlined. AdPSA prime vaccination was followed by VRP/PSA booster vaccination, inducing the highest number of anti-PSA T cells as shown in column 1.

What is claimed:

1. A method of producing an increased prostate cancer protective response in a subject having cancer through a prime/boost vaccine regime, the method comprising,
   a) administering a first vaccine comprising a serotype 5 adenovirus (Ad5) vector comprising prostate specific antigen (PSA), and
   b) after a period of time sufficient for the subject to generate an immune response to a), administering one or more second vaccines comprising an alphavirus replicon particle (VRP) comprising RNA comprising or produced from said prostate specific antigen, wherein said VRP is a TC-83 based alphavirus vector,
   wherein administration of said first and at least one second vaccines produces a prostate cancer protective response in said subject, and wherein said response is increased compared to the protective response elicited with a similar prime/boost vaccine regime wherein the VRP of part b) is the priming vaccine and the Ad5 of part a) is the at least one boosting vaccine.

2. The method of claim 1, wherein said protective response comprises reducing growth of prostate tumors.

3. The method of claim 1, wherein said protective response comprises elimination of prostate cancer tumors.

4. The method of claim 1, wherein said second vaccine is administered three times.

5. A method for treating a prostate cancer in a subject through a prime/boost vaccine regime, the method comprising,
   a) administering a first vaccine comprising a serotype 5 adenovirus (Ad5) vector comprising prostate specific antigen (PSA); and
   b) after a period of time sufficient for the subject to generate an immune response to a), administering one or more second vaccines comprising an alphavirus RNA replicon particle comprising RNA comprising or produced from said prostate specific antigen, wherein said VRP is a TC-83 based alphavirus vector, and
   wherein administration of said first and at least one second vaccines produces a prostate cancer protective response in said subject;
   wherein said response is increased compared to the protective response elicited with a similar prime/boost vaccine regime wherein the VRP of part b) is the priming vaccine and the Ad5 of part a) is the at least one boosting vaccine.

6. The method of claim 5, wherein said protective response comprises reducing growth of prostate tumors.

7. The method of claim 5, wherein said protective response comprises elimination of prostate cancer tumors.

8. The method of claim 5, wherein said second vaccine is administered three times.

9. A method of vaccination of a subject having cancer with a prime/boost vaccine regime, said method comprising,
   a) administering a first vaccine comprising an adenovirus vector comprising prostate specific antigen (PSA); and
   b) after a period of time sufficient for the subject to generate an immune response to a), administering one or more second vaccines comprising an alphavirus replicon particle comprising RNA comprising or produced from said prostate specific antigen, wherein said VRP is a TC-83 based alphavirus vector, and wherein administration of said first and at least one second vaccines produces a prostate cancer protective response in said subject;
   wherein said response is increased compared to the protective response elicited with a similar prime/boost vaccine regime wherein the VRP of part b) is the priming vaccine and the Ad5 of part a) is the at least one boosting vaccine.

10. The method of claim 9, wherein said protective response comprises reducing growth of prostate tumors.

11. The method of claim 9, wherein said protective response comprises elimination of prostate cancer tumors.

12. The method of claim 9, wherein at said second vaccine is administered three times.

13. The method of claim 1, wherein the period of time sufficient for the subject to generate an immune response to a) is at least about 14 days.

14. The method of claim 5, wherein the period of time sufficient for the subject to generate an immune response to a) is at least about 14 days.

15. The method of claim 9, wherein the period of time sufficient for the subject to generate an immune response to a) is at least about 14 days.

\* \* \* \* \*

SEQUENCE LISTING

```
<160> NUMBER OF SEQ ID NOS: 1

<210> SEQ ID NO 1
<211> LENGTH: 5873
<212> TYPE: DNA
<213> ORGANISM: Homo sapiens

<400> SEQUENCE: 1
ggtgtcttag gcacactggt cttggagtgc aaaggatcta ggcacgtgag gctttgtatg      60
aagaatcggg gatcgtaccc accccctgtt tctgtttcat cctgggcatg tctcctctgc     120
ctttgtcccc tagatgaagt ctccatgagc tacaagggcc tggtgcatcc agggtgatct     180
agtaattgca gaacagcaag tgctagctct ccctcccctt ccacagctct gggtgtggga     240
```

```
gggggttgtc cagcctccag cagcatgggg agggccttgg tcagcctctg ggtgccagca    300 gggcagggc ggagtcctgg ggaatgaagg ttttataggg ctcctgggg aggctcccca     360 gccccaagct taccacctgc acccggagag ctgtgtcacc atgtgggtcc cggttgtctt    420
cctcaccctg tccgtgacgt ggattggtga gaggggccat ggttgggggg atgcaggaga   480
gggagccagc cctgactgtc aagctgaggc tctttccccc ccaacccagc accccagccc   540
agacagggag ctgggctctt ttctgtctct cccagcccca cttcaagccc ataccccag    600 tccctccat attgcaacag tcctcactcc cacaccaggt cccgctccc tcccacttac     660 cccagaactt tcttcccatt tgcccagcca gctccctgct cccagctgct ttactaaagg   720
ggaagttcct gggcatctcc gtgtttctct tgtgggct caaaacctcc aaggacctct     780
ctcaatgcca ttggttcctt ggaccgtatc actggtccat ctcctgagcc cctcaatcct   840
atcacagtct actgactttt cccattcagc tgtgagtgtc caaccctatc ccagagacct   900
tgatgcttgg cctcccaatc ttgccctagg atacccagat gccaaccaga cacctccttc   960
tttcctagcc aggctatctg gcctgagaca caaatgggt ccctcagtct ggcaatggga   1020
ctctgagaac tcctcattcc ctgactctta gccccagact cttcattcag tggcccacat   1080
tttccttagg aaaaacatga gcatccccag ccacaactgc cagctctctg agtccccaaa   1140
tctgcatcct tttcaaaacc taaaaacaaa agaaaaaaca aataaaacaa aaccaactca   1200
gaccagaact gttttctcaa cctgggactt cctaaacttt ccaaaacctt cctcttccag   1260
caactgaacc tcgccataag gcacttatcc ctggttccta gcaccccta tccctcaga    1320 atccacaact tgtaccaagt ttcccttctc ccagtccaag accccaaatc accacaaagg   1380
acccaatccc cagactcaag atatggtctg ggcgctgtct tgtgtctcct accctgatcc   1440
ctgggttcaa ctctgctccc agagcatgaa gcctctccac cagcaccagc caccaacctg   1500
caaacctagg gaagattgac agaattccca gcctttccca gctcccctg cccatgtccc    1560 aggactccca gccttggttc tctgcccccg tgtcttttca aacccacatc ctaaatccat   1620
ctcctatccg agtcccccag ttcccctgt caaccctgat tccctgatc tagcacccc    1680 tctgcaggcg ctgcgcccct catcctgtct cggattgtgg gaggctggga gtgcgagaag   1740
cattcccaac cctggcaggt gcttgtggcc tctcgtggca gggcagtctg cggcggtgtt   1800
ctggtgcacc cccagtgggt cctcacagct gcccactgca tcaggaagtg agtaggggcc   1860
tggggtctgg ggagcaggtg tctgtgtccc agaggaataa cagctgggca ttttccccag   1920
gataacctct aaggccagcc ttgggactgg gggagagagg gaaagttctg gttcaggtca   1980 catgggagg cagggttggg gctggaccac cctccccatg gctgcctggg tctccatctg   2040
tgtccctcta tgtctctttg tgtcgctttc attatgtctc ttggtaactg gcttcggttg   2100
tgtctctccg tgtgactatt ttgttctctc tctccctctc ttctctgtct tcagtctcca   2160
tatctccccc tctctctgtc cttctctggt ccctctctag ccagtgtgtc tcaccctgta   2220
tctctctgcc aggctctgtc tctcggtctc tgtctcacct gtgccttctc cctactgaac   2280
acacgcacgg gatgggcctg ggggaccctg agaaaaggaa gggctttggc tgggcgcggt   2340
ggctcacacc tgtaatccca gcactttggg aggccaagga aggtagatca cctgaggtca   2400
ggagttcgag accagcctgg ccaactggtg aaaccccatc tctactaaaa atacaaaaaa   2460
ttagccaggc gtggtggcgc atgcctgtag tcccagctac tcaggagctg agggaggaga   2520
attgcattga acctggaggt tgaggttgca gtgagccgag accgtgccac tgcactccag   2580
```

```
cctgggtgac agagtgagac tccgcctcaa aaaaaaaaaa aaaaaaaaaa aaaaaaaga    2640 aaagaaaaga aaagaaaagg aagtgttttta tccctgatgt gtgtgggtat gagggtatga   2700
gagggcccct ctcactccat tccttctcca ggacatccct ccactcttgg gagacacaga   2760
gaagggctgg ttccagctgg agctgggagg ggcaattgag ggaggaggaa ggagaagggg   2820
gaaggaaaac agggtatggg ggaaaggacc ctggggagcg aagtggagga tacaaccttg   2880
ggcctgcagg caggctacct acccacttgg aaacccacgc caaagccgca tctacagctg   2940
agccactctg aggcctcccc tccccggcgg tccccactca gctccaaagt ctctctccct   3000
tttctctccc acactttatc atcccccgga ttcctctcta cttggttctc attcttcctt   3060
tgacttcctg cttcccttc tcattcatct gtttctcact ttctgcctgg ttttgttctt    3120
ctctctctct ttctctggcc catgtctgtt tctctatgtt tctgtctttt ctttctcatc   3180
ctgtgtattt tcggctcacc ttgtttgtca ctgttctccc ctctgccctt tcattctctc   3240 tgcccttta ccctcttcct tttcccttgg ttctctcagt tctgtatctg cccttcaccc     3300
tctcacactg ctgtttccca actcgttgtc tgtattttgg cctgaactgt gtcttcccaa   3360
ccctgtgttt tctcactgtt tctttttctc ttttggagcc tcctccttgc tcctctgtcc   3420
cttctctctt tccttatcat cctcgctcct cattcctgcg tctgcttcct ccccagcaaa   3480
agcgtgatct tgctgggtcg gcacagcctg tttcatcctg aagacacagg ccaggtattt   3540
caggtcagcc acagcttccc acacccgctc tacgatatga gcctcctgaa gaatcgattc   3600
ctcaggccag gtgatgactc cagccacgac ctcatgctgc tccgcctgtc agagcctgcc   3660
gagctcacgg atgctgtgaa ggtcatggac ctgcccaccc aggagccagc actggggacc   3720
acctgctacg cctcaggctg gggcagcatt gaaccagagg agtgtacgcc tgggccagat   3780
ggtgcagccg ggagcccaga tgcctgggtc tgagggagga gggacagga ctcctgggtc    3840 tgagggagga gggccaagga accaggtggg gtccagccca caacagtgtt tttgcctggc   3900
ccgtagtctt gaccccaaag aaacttcagt gtgtggacct ccatgttatt tccaatgacg   3960
tgtgtgcgca agttcaccct cagaaggtga ccaagttcat gctgtgtgct ggacgctgga   4020 caggggggcaa aagcacctgc tcggtgagtc atccctactc ccaagatctt gagggaaagg   4080
tgagtgggac cttaattctg ggctggggtc tagaagccaa caaggcgtct gcctcccctg   4140
ctccccagct gtagccatgc cacctcccg tgtctcatct cattccctcc ttccctcttc    4200
tttgactccc tcaaggcaat aggttattct tacagcacaa ctcatctgtt cctgcgttca   4260
gcacacggtt actaggcacc tgctatgcac ccagcactgc cctagagcct gggacatagc   4320
agtgaacaga cagagagcag cccctccctt ctgtagcccc caagccagtg aggggcacag   4380
gcaggaacag ggaccacaac acagaaaagc tggaggtgt caggaggtga tcaggctctc    4440
ggggagggag aaggggtggg gagtgtgact gggaggagac atcctgcaga aggtgggagt   4500
gagcaaacac ctgcgcaggg gaggggaggg cctgcggcac ctgggggagc agagggaaca   4560
gcatctggcc aggcctggga ggaggggcct agagggcgtc aggagcagag aggaggttgc   4620
ctggctggag tgaaggatcg gggcagggtg cgagagggaa caaaggaccc ctcctgcagg   4680
gcctcacctg ggccacagga ggacactgct tttcctctga ggagtcagga actgtggatg   4740
gtgctggaca gaagcaggac agggcctggc tcaggtgtcc agaggctgcg ctggcctcct   4800
atgggatcag actgcaggga gggagggcag cagggatgtg gagggagtga tgatgggct    4860 gacctgggggg tggctccagg cattgtcccc acctgggccc ttaccagcc tccctcacag   4920 gctcctggcc ctcagtctct cccctccact ccattctcca cctacccaca gtgggtcatt   4980
```

```
ctgatcaccg aactgaccat gccagccctg ccgatggtcc tccatggctc cctagtgccc    5040
tggagaggag gtgtctagtc agagagtagt cctggaaggt ggcctctgtg aggagccacg    5100
gggacagcat cctgcagatg gtcctggccc ttgtcccacc gacctgtcta caaggactgt    5160
cctcgtggac cctcccctct gcacaggagc tggaccctga agtcccttcc taccggccag    5220
gactggagcc cctaccccte tgttggaatc cctgcccacc ttcttctgga agtcggctct    5280
ggagacattt ctctcttctt ccaaagctgg gaactgctat ctgttatctg cctgtccagg    5340
tctgaaagat aggattgccc aggcagaaac tgggactgac ctatctcact ctctccctgc    5400
ttttaccctt agggtgattc tgggggccca cttgtctgta atggtgtgct tcaaggtatc    5460
acgtcatggg gcagtgaacc atgtgccctg cccgaaaggc cttccctgta caccaaggtg    5520
gtgcattacc ggaagtggat caaggacacc atcgtggcca acccctgagc accctatca    5580 agtccctatt gtagtaaact tggaaccttg gaaatgacca ggccaagact caagcctccc    5640
cagttctact gacctttgtc cttaggtgtg aggtccaggg ttgctaggaa aagaaatcag    5700
cagacacagg tgtagaccag agtgtttctt aaatggtgta attttgtcct ctctgtgtcc    5760
tggggaatac tggccatgcc tggagacata tcactcaatt tctctgagga cacagttagg    5820
atggggtgtc tgtgttattt gtgggataca gagatgaaag aggggtggga tcc           5873
```